United States Patent
Yoshikawa et al.

(10) Patent No.: US 9,315,433 B2
(45) Date of Patent: Apr. 19, 2016

(54) METHOD FOR PRODUCING 2,7-OCTADIEN-1-OL

(71) Applicant: KURARAY CO., LTD., Kurashiki-shi (JP)

(72) Inventors: Tatsuya Yoshikawa, Kamisu (JP); Tomoaki Tsuji, Kamisu (JP)

(73) Assignee: KURARAY CO., LTD., Kurashiki-shi (JP)

(*) Notice: Subject to any disclaimer, the term of this patent is extended or adjusted under 35 U.S.C. 154(b) by 0 days.

(21) Appl. No.: 14/778,798

(22) PCT Filed: Mar. 26, 2014

(86) PCT No.: PCT/JP2014/058663
§ 371 (c)(1),
(2) Date: Sep. 21, 2015

(87) PCT Pub. No.: WO2014/157402
PCT Pub. Date: Oct. 2, 2014

(65) Prior Publication Data
US 2016/0046549 A1 Feb. 18, 2016

(30) Foreign Application Priority Data
Mar. 27, 2013 (JP) .................. 2013-067269

(51) Int. Cl.
*C07C 29/46* (2006.01)
*C07C 29/36* (2006.01)
*C07C 29/86* (2006.01)
*C07C 33/02* (2006.01)
*C07C 31/36* (2006.01)

(52) U.S. Cl.
CPC ............. *C07C 29/46* (2013.01); *C07C 29/86* (2013.01); *C07C 29/36* (2013.01); *C07C 31/36* (2013.01); *C07C 33/02* (2013.01)

(58) Field of Classification Search
CPC ........ C07C 29/36; C07C 33/02; C07C 29/46; C07C 31/36
USPC ............................. 568/909.5, 845
See application file for complete search history.

(56) References Cited

U.S. PATENT DOCUMENTS

| 5,057,631 A | 10/1991 | Tokitoh et al. |
| 5,345,007 A | 9/1994 | Monflier et al. |

FOREIGN PATENT DOCUMENTS

| JP | 54-144306 A | 11/1979 |
| JP | 64-25738 A | 1/1989 |
| JP | 64-25739 A | 1/1989 |
| JP | 3-232831 A | 10/1991 |
| JP | 5-221897 A | 8/1993 |
| JP | 6-321828 | 11/1994 |
| JP | 8-501800 A | 2/1996 |
| JP | 11-189556 A | 7/1999 |
| JP | 11-228469 A | 8/1999 |
| JP | 2008-247836 A | 10/2008 |

OTHER PUBLICATIONS

Eric Monflier, et al., "Highly efficient telomerization of butadiene into octadienol in a micellar system: a judicious choice of the phosphine/surfactant combination," Applied Catalysis A: General, vol. 131, 1995, pp. 167-178.

Byoung In Lee, et al., "The effects of reaction variables on the palladium-catalyzed reactions of butadiene with water," Journal of Molecular Catalysis A: Chemical, vol. 166, 2001, pp. 233-242.

International Search Report issued May 13, 2014 in PCT/JP2014/058663 filed Mar. 26, 2014.

*Primary Examiner* — Elvis O Price
(74) *Attorney, Agent, or Firm* — Oblon, McClelland, Maier & Neustadt, L.L.P

(57) ABSTRACT

Provided is a simple and industrially advantageous method for producing 2,7-octadien-1-ol, in which an expensive palladium catalyst is recovered in high efficiency and the reaction rate per atom of palladium is enhanced. Specifically, provided is a method for producing 2,7-octadien-1-ol by subjecting butadiene and water to a telomerization in the presence of a palladium catalyst containing a water-soluble triarylphosphine having two or more sulfonate groups in the molecule and a palladium compound, a tertiary amine, and carbon dioxide, including a step of mixing the telomerization solution obtained by the telomerization with an organic solvent having a dielectric constant at 25° C. of 2 to 18, followed by carrying out phase separation in the presence of carbon dioxide, thereby obtaining 2,7-octadien-1-ol from an organic phase while recovering an aqueous phase including the palladium catalyst. By this production method, the selectivity for 2,7-octadien-1-ol is enhanced.

13 Claims, No Drawings

US 9,315,433 B2

METHOD FOR PRODUCING 2,7-OCTADIEN-1-OL

TECHNICAL FIELD

The present invention relates to a method for producing 2,7-octadien-1-ol. More specifically, the present invention relates to a method for producing 2,7-octadien-1-ol by reacting butadiene with water in the presence of a palladium catalyst or the like.

BACKGROUND ART 2,7-Octadien-1-ol can be derived into 7-octenal by an isomerization reaction and the 7-octenal can be derived into 1,9-nonanedial by a hydroformylation reaction. From the viewpoint that the 1,9-nonanedial can be derived into 1,9-nonanediamine which is useful as a raw material of a monomer for a polymer by a reductive amination reaction, the 2,7-octadien-1-ol is of a high industrial value and it is important to develop a method for producing the same.

As a method for producing 2,7-octadien-1-ol by subjecting butadiene and water to a telomerization in the presence of a palladium catalyst containing a palladium compound and an organic phosphorus compound, carbon dioxide, and a tertiary amine, the following methods are known.

(1) A method for producing an alkadienol, in which a conjugated alkadiene and water are subjected to a telomerization in the presence of a palladium catalyst containing a palladium compound and an organic phosphorus compound, a tertiary amine, and an organic solvent having high solubility in water, the obtained telomerization solution is distilled to extract an alkadienol and the solvent, while a solution containing the palladium catalyst is obtained from the bottom liquid of a column, and the solution containing the palladium catalyst is cycled and used in the reaction (see PTLs 1 to 4, and the like), (2) a method for producing 2,7-octadien-1-ol, in which butadiene and water are subjected to a telomerization in the presence of a palladium catalyst containing a palladium compound and water-soluble phosphine in an aqueous sulfolane solution including carbonate of a tertiary amine and a bicarbonate to generate 2,7-octadien-1-ol, at least part of the reaction mixed liquid is extracted with a saturated aliphatic hydrocarbon or the like to separate the 2,7-octadien-1-ol by extraction, and at least a part of the sulfolane extract including the palladium catalyst is cycled and used in the reaction (see PTLs 5 to 7, and the like), and (3) a method for producing 2,7-octadien-1-ol by subjecting butadiene and water to a telomerization, in which a tertiary amine having a function as a surfactant capable of compensating for a low reaction rate due to low solubility of butadiene in water is coexistent in a two-phase system including an aqueous phase having a palladium catalyst containing a palladium compound and a water-soluble phosphorus-containing compound dissolved in water and an organic phase which is butadiene (see PTL 8, NPL 1, and the like).

CITATION LIST

Patent Literature

[PTL 1] JP-A-S54-144306
[PTL 2] JP-A-H05-221897
[PTL 3] JP-A-H11-189556
[PTL 4] JP-A-H11-228469
[PTL 5] JP-A-S64-25739
[PTL 6] JP-A-H03-232831
[PTL 7] JP-A-H06-321828
[PTL 8] JP-T-H08-501800

Non Patent Literature

[NPL 1] Applied Catalysis A: General, vol. 131, 1995, pp. 167-178
[NPL 2] Journal of Molecular Catalysis A: Chemical, vol. 166, 2001, pp. 233-242

SUMMARY OF INVENTION

Technical Problem

In the production method (1) described in PTLs 1 to 4, when the obtained telomerization solution is distilled, a solution containing a palladium catalyst is recovered from the bottom liquid in a column. In order to inhibit the metalation of the palladium catalyst, it is necessary to carry out distillation at 110° C. or lower under reduced pressure. In this case, the palladium catalyst and 2,7-octadien-1-ol necessarily coexist under the conditions of low concentration of carbon dioxide in a system. In a case where butadiene and a palladium catalyst coexist in the absence of carbon dioxide or in the presence of carbon dioxide at a low concentration, 1,3,7-octatriene, oligomers, and the like are generated (see NPL 2). Further, since the palladium catalyst coexists with a tertiary amine, which is a basic compound, in the absence of carbon dioxide or in the presence of carbon dioxide at a low concentration and the stability of a palladium complex is thus impaired, catalyst deactivation is inevitable by metalation of palladium in a case where the distillation temperature, the distillation time, the composition of a chemical liquid inside a distillation column, and the like can be strictly controlled. Accordingly, a method of recovering most of the palladium catalyst while not heating is required.

In the production method (2) described in PTLs 5 to 7, 2,7-octadien-1-ol is extracted by adding a saturated aliphatic hydrocarbon to a telomerization solution, and it is thus necessary to install equipment for distillation and recovery of the saturated aliphatic hydrocarbon itself, which results in an increase in cost burden related to the equipment. Further, sulfolane is more expensive than a hydrocarbon-based solvent, typically such as hexane, and accordingly, it is necessary to recover the sulfolane by subjecting the 2,7-octadien-1-ol phase obtained by extraction to water washing, for example. In addition, the sulfolane is a sulfur atom-containing substance, and in a case of incineration disposal of the sulfolane, an incinerator having desulfurization equipment is required. Therefore, there is a demand for a method for conveniently recovering most of a palladium catalyst after a telomerization while not using sulfolane in the telomerization.

The production method (3) described in PTL 8 and NPL 1, dimethyldodecylamine, for example, is used as a tertiary amine. Since the dimethyldodecylamine has a function as a surfactant, complicated operations such as multiple extraction and recovery, or distillation and separation are required so as to increase the recovery of a tertiary amine. Further, according to Examples, the method can be said to be a method having low selectivity for 2,7-octadien-1-ol. Accordingly, as a method in which a tertiary amine to be easily recovered can be used, a method having high selectivity for 2,7-octadien-1-ol is also demanded.

That is, it is an object of the present invention to provide a simple and industrially advantageous method for producing 2,7-octadien-1-ol, in which an expensive palladium catalyst is recovered at high efficiency, thereby improving a reaction rate per atom of palladium, and further, to improve the selectivity for 2,7-octadien-1-ol.

Solution to Problem

The present inventors have conduced intensive studies, and as a result, they have found that it is possible to perform phase separation in the presence of carbon dioxide, and thus recover the palladium catalyst from the aqueous phase in high efficiency by mixing the obtained telomerization solution with an organic solvent having a specific dielectric constant in a telomerization of butadiene with water, in the presence of a palladium catalyst containing a water-soluble triarylphosphine having two or more sulfonate groups in the molecule and a palladium compound, a tertiary amine, and carbon dioxide, and in the absence of an organic solvent such as sulfolane.

In addition, it has been found that by using a palladium catalyst formed by using a specific water-soluble triarylphosphine, the recovery of the palladium catalyst is further improved and the selectivity of the telomerization is also improved.

The present invention has been completed based on the above findings.

That is, the present invention relates to [1] to [13] below.

[1] A method for producing 2,7-octadien-1-ol by subjecting butadiene and water to a telomerization in the presence of a palladium catalyst containing a water-soluble triarylphosphine having two or more sulfonate groups in the molecule and a palladium compound, a tertiary amine, and carbon dioxide, including a step of:

mixing the telomerization solution obtained by the telomerization with an organic solvent having a dielectric constant of 2 to 18 at 25° C., followed by carrying out phase separation in the presence of carbon dioxide, thereby obtaining 2,7-octadien-1-ol from an organic phase while recovering an aqueous phase including the palladium catalyst.

[2] The method for producing 2,7-octadien-1-ol as described in [1], in which the water-soluble triarylphosphine is represented by the following general formula (I);

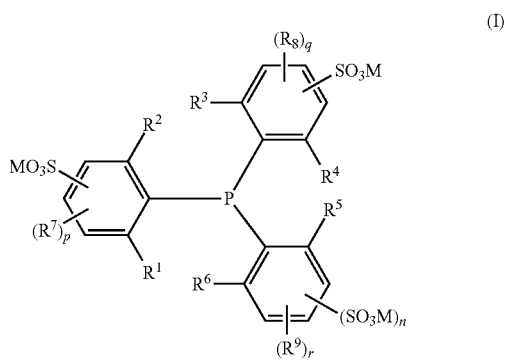

wherein $R^1$, $R^2$, $R^3$, $R^4$, $R^5$, and $R^6$ each independently represent a hydrogen atom, an alkyl group having 1 to 4 carbon atoms, or an alkoxy group having 1 to 4 carbon atoms; $R^7$, $R^8$, and $R^9$ each independently represent an alkyl group having 1 to 4 carbon atoms or an alkoxy group having 1 to 4 carbon atoms; p, q, and r each independently represent an integer of 0 to 2; M's may be the same as or different from each other, and represent a cation of a metal atom belonging to Group 1 or an ammonium cation derived from a tertiary amine, in which the total number of carbon atoms of a group bonded to one atom of nitrogen is 3 to 27; n represents 0 or 1; and the binding positions of sulfonate groups (—$SO_3M$) are all the meta-positions or the para-positions to phosphorous atoms.

[3] The method for producing 2,7-octadien-1-ol as described in [2], in which in General Formula (I), $R^1$, $R^3$, $R^5$, $R^7$, $R^8$, and $R^9$ each independently represent a hydrogen atom, a methyl group, or a methoxy group, $R^2$, $R^4$, and $R^6$ are all hydrogen atoms, M's each independently represent a cation of an alkali metal atom or an ammonium cation derived from a tertiary amine, in which the total number of carbon atoms of a group bonded to one atom of nitrogen is 3 to 27, and the binding positions of sulfonate groups (—$SO_3M$) are all the meta-positions to phosphorous atoms.

[4] The method for producing 2,7-octadien-1-ol as described in [2], in which in General Formula (I), $R^1$, $R^2$, $R^3$, $R^4$, $R^5$, and $R^6$ each independently represent a hydrogen atom, a methyl group, or a methoxy group, p, q, and r are all 0, M's each independently represent a cation of a lithium atom, a cation of a sodium atom, a cation of a potassium atom, or an ammonium cation derived from a tertiary amine, in which the total number of carbon atoms of a group bonded to one atom of nitrogen is 3 to 27, and the binding positions of sulfonate groups (—$SO_3M$) are each the diagonal positions of $R^1$, $R^3$, or $R^5$ on the benzene ring.

[5] The method for producing 2,7-octadien-1-ol as described in [4], in which in General Formula (I), $R^1$, $R^3$, and $R^5$ are all the same as each other and represent a hydrogen atom or a methyl group, p, q, and r are all 0, and M's are the same as each other and represent a cation of a lithium atom, a cation of a sodium atom, a cation of a potassium atom, or an ammonium cation derived from a tertiary amine, in which the total number of carbon atoms of a group bonded to one atom of nitrogen is 3 to 27.

[6] The method for producing 2,7-octadien-1-ol as described in [1], in which in General Formula (I), at least two of $R^1$, $R^3$, and $R^5$ are each an alkyl group having 1 to 4 carbon atoms or an alkoxy group having 1 to 4 carbon atoms.

[7] The method for producing 2,7-octadien-1-ol as described in [6], in which at least two of $R^1$, $R^3$, and $R^5$ are a methyl group.

[8] The method for producing 2,7-octadien-1-ol as described in any one of [1] to [7], in which in General Formula (I), M is an ammonium cation derived from a tertiary amine, in which the total number of carbon atoms of a group bonded to one atom of nitrogen is 5 to 24.

[9] The method for producing 2,7-octadien-1-ol as described in [8], in which M is an ammonium cation derived from a tertiary amine, in which the total number of carbon atoms of a group bonded to one atom of nitrogen is 5 to 7.

[10] The method for producing 2,7-octadien-1-ol as described in any one of [1] to [9], in which the phase separation is carried out under the conditions of 130° C. or lower and a total pressure after introduction of carbon dioxide of 0.1 MPa (gauge pressure) or more.

[11] The method for producing 2,7-octadien-1-ol as described in [10], in which the phase separation is carried out at 5° C. to 90° C., and a total pressure after introduction of carbon dioxide of 0.5 MPa to 3 MPa (gauge pressure).

[12] The method for producing 2,7-octadien-1-ol as described in any one of [1] to [11], in which the telomerization is carried out under the conditions of 130° C. or lower and a total pressure after introduction of carbon dioxide of 0.5 MPa (gauge pressure) or more.

[13] The method for producing 2,7-octadien-1-ol as described in any one of [1] to [12], in which at least a part of the aqueous phase including the recovered palladium catalyst is reused in the telomerization.

Advantageous Effects of Invention

Since by the production method of the present invention, most of the palladium catalyst can be recovered while not heating, and further, it is not necessary to use sulfolane and an easily recoverable tertiary amine can be used, and it is possible to provide a convenient and industrially advantageous method for producing 2,7-octadien-1-ol.

In addition, for example, by using a palladium catalyst formed by using a water-soluble triarylphosphine having two or more aryl groups having a substituent in the ortho-position, the recovery of the palladium catalyst can further be improved and the selectivity of the telomerization can also be improved.

DESCRIPTION OF EMBODIMENTS

Method for Producing 2,7-Octadien-1-ol

The present invention is directed to a method for producing 2,7-octadien-1-ol by subjecting butadiene and water to a telomerization in the presence of a palladium catalyst containing a water-soluble triarylphosphine having two or more sulfonate groups in the molecule and a palladium compound, a tertiary amine, and carbon dioxide, including a step of mixing the telomerization solution obtained by the telomerization with an organic solvent having a dielectric constant of 2 to 18 at 25° C., followed by carrying out phase separation in the presence of carbon dioxide, and then 2,7-octadien-1-ol is obtained from an organic phase while recovering an aqueous phase including the palladium catalyst.

Here, in the present specification, the restrictive wording with "being preferable" can be arbitrarily adopted and a combination of restrictive wordings with "being preferable" can be said to be more preferred.

Hereinafter, the method for producing 2,7-octadien-1-ol of the present invention will be described with reference to the following steps in order.

[1. Palladium Catalyst Preparing Step]
A step of preparing a palladium catalyst from a water-soluble triarylphosphine having two or more sulfonate groups in the molecule (hereinafter sometimes simply referred to as a water-soluble triarylphosphine) and a palladium compound.

[2. Telomerization Step]
A step of obtaining 2,7-octadien-1-ol by reacting butadiene and water in the presence of a palladium catalyst, a tertiary amine, and carbon dioxide.

[3. Catalyst Recovering Step and Product Separating Step]
A step of obtaining 2,7-octadien-1-ol from the organic phase by mixing the telomerization solution obtained in the telomerization step and an organic solvent having a dielectric constant of 2 to 18 at 25° C., followed by carrying out phase separation in the presence of carbon dioxide (product separating step), and a step of recovering the aqueous phase including the palladium catalyst in high efficiency (catalyst recovering step).

Here, the "palladium catalyst" for use in the present invention includes those consisting of a palladium compound and a water-soluble triarylphosphine as described later, as well as a free water-soluble triarylphosphine not coordinated with palladium.

The "telomerization solution" obtained by the telomerization contains 2,7-octadien-1-ol, 1,7-octadien-3-ol, 1,3,6-octatriene, 1,3,7-octatriene, 2,4,6-octatriene, 4-vinylcyclohexene, and the like which are products or by-products, in addition to the tertiary amine, carbon dioxide, butadiene, and water, used in the telomerization, and may additionally contain a solvent for use in preparation of a palladium catalyst and/or a telomerization.

Moreover, in the present invention, an organic solvent having a dielectric constant of 2 to 18 at 25° C. is used. For example, it is described that the dielectric constant of a solvent varies depending on the temperature in Journal of Chemical Thermodynamics, 2011, vol. 43, pp. 569-575. Further, it is known that even in a case where a dielectric constant is measured using a solvent sufficiently purified under the same temperature, the value varies with a trace amount of impure materials of the solvent or depending on the type of a measurement device (see, for example, Fluid Phase Equilibria, 2009, vol. 277, pp. 20-28). Also, according to the investigation of the present inventors, it seems that there is an error of about 3% in the measured values. Here, as a dielectric constant of an organic solvent at 25° C. as mentioned in the present invention, the numeral values described in International Journal of Pharmaceutics, 2004, vol. 283, pp. 117-125; and Journal of Power Sources, 1989, vol. 26, pp. 9-21 are used. In the present specification, the dielectric constant at 25° C. is defined to be 2 to 18, but it is in a numeral value range taking into consideration of an error of 3%. In addition, unless otherwise specified, the dielectric constant in the present specification is a numeral value at 25° C.

[1. Palladium Catalyst Preparing Step]
It is described that the telomerization of the conjugated alkadiene can be carried out with a palladium catalyst formed by coordination of one or more molecules of a trivalent phosphorus-containing compound with one atom of 0-valent palladium in, for example, Journal of Molecular Catalysis A: Chemical, vol. 144, 1999, pp. 27-40.

Various conditions and the like for preparation of the palladium catalyst will be described below.

(Palladium Compound)

The form and the atomic value state of the palladium compound are not particularly limited, but the palladium compound may not form a salt and may be 0-valent or divalent.

Preferable examples of the 0-valent palladium compound include bis(t-butylisonitrile)palladium (0), bis(t-amylisonitrile)palladium (0), bis(cyclohexylisonitrile)palladium (0), bis(phenylisonitrile)palladium (0), bis(p-tolylisonitrile)palladium (0), bis(2,6-dimethylphenylisonitrile)palladium (0), tris(dibenzylideneacetone)dipalladium (0), (1,5-cyclooctadiene) (maleic anhydride)palladium (0), bis(norbornene) (maleic anhydride)palladium (0), bis(maleic anhydride) (norbornene)palladium (0), (dibenzylideneacetone)(bipyridyl)palladium (0), (p-benzoquinone)(o-phenanthroline)palladium (0), tetrakis(triphenylphosphine)palladium (0), tris(triphenylphosphine)palladium (0), bis(tritolylphosphine)palladium (0), bis(trixylylphosphine)palladium (0), bis(trimesitylphosphine)palladium (0), bis(tritetramethylphenyl)palladium (0), and bis(trimethylmethoxyphenylphosphine)palladium (0).

Preferable examples of the divalent palladium compound include palladium chloride (II), palladium nitrate (II), tetramine dichloropalladium (II), disodium tetrachloropalladium (II), palladium acetate (II), palladium benzoate (II), palladium α-picolinate (II), bis(acetylacetone)palladium (II), bis(8-oxyquinoline)palladium (II), bis(allyl)palladium (II), (η-cyclopentadienyl)palladium (II), (η-cyclopentadienyl)(1,5-cyclooctadiene)palladium (II) tetrafluoroborate, bis(benzonitrile)palladium (II) acetate, di-µ-chloro-dichlorobis(tripnylphosphine)dipalladium (II), bis(tri-n-butylphosphine)palladium (II) acetate, and 2,2'-bipyridyl palladium (II) acetate.

Among these, from the viewpoints of easy industrial availability and cost, tetrakis(triphenylphosphine)palladium (0), palladium acetate (II), and bis(acetylacetone)palladium (II) are more preferred, and palladium acetate (II) and bis(acetylacetone)palladium (II) are still more preferred.

The palladium compounds may be used singly or as a mixture of two or more kinds thereof.

(Water Soluble Triarylphosphine)

It is known that a palladium catalyst used can be recovered after a reaction by using a water-soluble triarylphosphine as a trivalent phosphorous-containing compound to be reacted with a palladium compound (see, for example, Chemical Review, vol. 109, 2009, pp. 643-710). In order to carry out a telomerization in an industrially advantageous manner, it is important to increase the catalytic activity per atom of palladium even in a reaction in the state in which an organic phase and an aqueous phase are homogeneous, as in the present invention.

The water-soluble triarylphosphine for use in the present invention is a water-soluble triarylphosphine having two or more sulfonate groups in the molecule, and from the viewpoint of increasing the catalytic activity per atom of palladium, water-soluble triarylphosphine represented by the following general formula (I) is preferred.

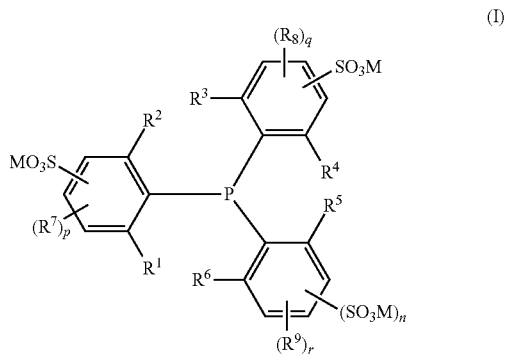

wherein $R^1$, $R^2$, $R^3$, $R^4$, $R^5$, and $R^6$ each independently represent a hydrogen atom, an alkyl group having 1 to 4 carbon atoms, or an alkoxy group having 1 to 4 carbon atoms; $R^7$, $R^8$, and $R^9$ each independently represent an alkyl group having 1 to 4 carbon atoms or an alkoxy group having 1 to 4 carbon atoms; p, q, and r each independently represent an integer of 0 to 2; M's may be the same as or different from each other, and represent a cation of a metal atom belonging to Group 1 or an ammonium cation derived from a tertiary amine, in which the total number of carbon atoms of a group bonded to one atom of nitrogen is 3 to 27; n represents 0 or 1; and the binding positions of sulfonate groups (—$SO_3M$) are all the meta-positions or the para-positions to phosphorous atoms.

Examples of the alkyl group having 1 to 4 carbon atoms include a methyl group, an ethyl group, an n-propyl group, an isopropyl group, an n-butyl group, an isobutyl group, an s-butyl group, and a t-butyl group. Among these, an alkyl group having 1 to 3 carbon atoms is preferred, a methyl group or an ethyl group is more preferred, and a methyl group is still more preferred.

Examples of the alkoxy group having 1 to 4 carbon atoms include those in which an alkyl moiety is the alkyl group. Among these, an alkoxy group having 1 to 3 carbon atoms is preferred, a methoxy group and an ethoxy group are more preferred, and a methoxy group is still more preferred.

Examples of the metal atom including the cation of a metal atom belonging to Group 1 include a lithium atom, a sodium atom, a potassium atom, a rubidium atom, and a cesium atom. Among these, a lithium atom, a sodium atom, and a potassium atom are preferred, and a sodium atom is more preferred.

Examples of the tertiary amine for use in formation of the ammonium cation derived from a tertiary amine, in which the total number of carbon atoms of a group bonded to one atom of nitrogen is 3 to 27, include trimethylamine, triethylamine, tripropylamine, triisopropylamine, tributylamine, triisobutylamine, tri-s-butylamine, tri-t-butylamine, tripentylamine, triisopentylamine, trineopentylamine, trihexylamine, triheptylamine, trioctylamine, triphenylamine, tribenzylamine, N,N-dimethylethylamine, N,N-dimethylpropylamine, N,N-dimethylisopropylamine, N,N-dimethylbutylamine, N,N-dimethylisobutylamine, N,N-dimethyl-s-butylamine, N,N-dimethyl-t-butylamine, N,N-dimethylpentylamine, N,N-dimethylisopentylamine, N,N-dimethylneopentylamine, N,N-dimethylhexylamine, N,N-dimethylheptylamine, N,N-dimethyloctylamine, N,N-dimethylnonylamine, N,N-dimethyldecylamine, N,N-dimethylundecylamine, N,N-dimethyldodecylamine, N,N-dimethylphenylamine, N,N-dimethylbenzylamine, N,N-diethylmonomethylamine, N,N-dipropylmonomethylamine, N,N-diisopropylmonomethylamine, N,N-dibutylmonomethylamine, N,N-diisobutylmonomethylamine, N,N-di-s-butylmonomethylamine, N,N-di-t-butylmonomethylamine, N,N-dipentylmonomethylamine, N,N-diisopentylmonomethylamine, N,N-dineopentylmonomethylamine, N,N-dihexylmonomethylamine, N,N-diheptylmonomethylamine, N,N-dioctylmonomethylamine, N,N-dinonylmonomethylamine, N,N-didecylmonomethylamine, N,N-diundecylmonomethylamine, N,N-didodecylmonomethylamine, N,N-diphenylmonomethylamine, N,N-dibenzylmonomethylamine, N,N-dipropylmonomethylamine, N,N-diisopropylmonoethylamine, N,N-dibutylmonoethylamine, N,N-diisobutylmonoethylamine, N,N-di-s-butylmonoethylamine, N,N-di-t-butylmonoethylamine, N,N-dipentylmonoethylamine, N,N-diisopentylmonoethylamine, N,N-dineopentylmonoethylamine, N,N-dihexylmonoethylamine, N,N-diheptylmonoethylamine, N,N-dioctylmonoethylamine, N,N-dinonylmonoethylamine, N,N-didecylmonoethylamine, N,N-diundecylmonoethylamine, N,N-didodecylmonoethylamine, N,N-diphenylmonoethylamine, and N,N-dibenzylmonoethylamine.

In the tertiary amine, the total number of carbon atoms of a group bonded to one atom of nitrogen is preferably 3 to 24, more preferably 5 to 24, still more preferably 5 to 10, and particularly preferably 5 to 7. Further, as the group bonded to one atom of nitrogen, an alkyl group, an aryl group, and an aryl-substituted alkyl group are preferred, and an alkyl group is more preferred.

Among those, as the tertiary amine, triethylamine, N,N-dimethylisopropylamine, and trioctylamine are preferred, and from the viewpoints of easy availability and production cost, triethylamine and N,N-dimethylisopropylamine are more preferred.

Particularly preferred is a water-soluble triarylphosphine, in which in General Formula (I), $R^1$, $R^3$, $R^5$, $R^7$, $R^8$, and $R^9$ each independently represent a hydrogen atom, a methyl group, or a methoxy group, $R^2$, $R^4$, and $R^6$ are all hydrogen atoms, M's each independently represent a cation of an alkali metal atom or an ammonium cation derived from a tertiary amine, in which the total number of carbon atoms of a group bonded to one atom of nitrogen is 3 to 27, and all of the binding positions of sulfonate groups (—SO$_3$M) are the meta-positions to phosphorous atoms.

Also preferred is a water-soluble triarylphosphine, in which in General Formula (I), $R^1$, $R^2$, $R^3$, $R^4$, $R^5$, and $R^6$ each independently represent a hydrogen atom, a methyl group, or a methoxy group, p, q, and r are all 0, M's each independently represent a cation of a lithium atom, a cation of a sodium atom, a cation of a potassium atom, or an ammonium cation derived from a tertiary amine, in which the total number of carbon atoms of a group bonded to one atom of nitrogen is 3 to 27, and the binding positions of sulfonate groups (—SO$_3$M) are each the diagonal positions of $R^1$, $R^3$, or $R^5$ on the benzene ring.

Still also preferred is a water-soluble triarylphosphine, in which in General Formula (I), $R^1$, $R^3$, and $R^5$ are all the same as each other and represent a hydrogen atom or a methyl group, p, q, and r are all 0, and M's are the same as each other and are each a cation of a lithium atom, a cation of a sodium atom, a cation of a potassium atom or an ammonium cation derived from a tertiary amine, in which the total number of carbon atoms of a group bonded to one atom of nitrogen is 3 to 27.

Furthermore, from the viewpoint of recovering and reusing the palladium catalyst used in the telomerization, tertiary amine for use in formation of an ammonium cation derived from a tertiary amine is not particularly limited, but the tertiary amine used in the telomerization, for example, is preferred. Further, from the viewpoints of further improving the recovery of the palladium catalyst and improving the selectivity of the telomerization, preferred is a water-soluble triarylphosphine, in which in General Formula (I), at least two of $R^1$, $R^3$, and $R^5$ are each an alkyl group having 1 to 4 carbon atoms or an alkoxy group having 1 to 4 carbon atoms.

Also preferred is a water-soluble triarylphosphine, in which in General Formula (I), at least two of $R^1$, $R^3$, and $R^5$ are a methyl group.

In any of the water-soluble triarylphosphine above, it is preferable that an M is an ammonium cation derived from a tertiary amine, in which the total number of carbon atoms of a group bonded to one atom of nitrogen is 5 to 24.

Specific examples of the compound of General Formula (I) include compounds represented by the following general formulae. Further, in the formulae, Me represents a methyl group. In each of the chemical structural formulae, n represents 0 or 1.

(I-1)
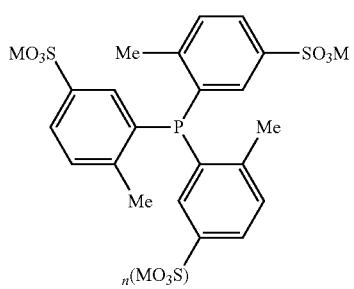

(I-2)
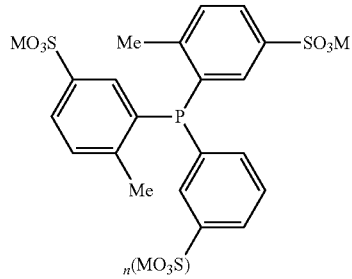

(I-3)
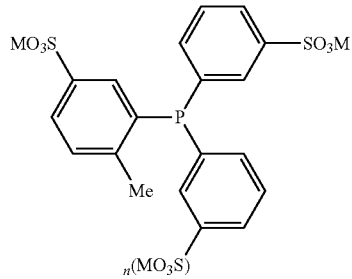

(I-4)
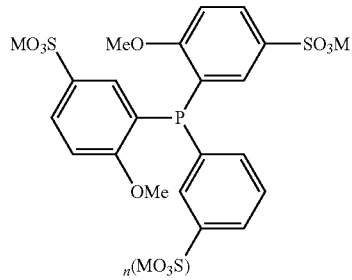

(I-5)
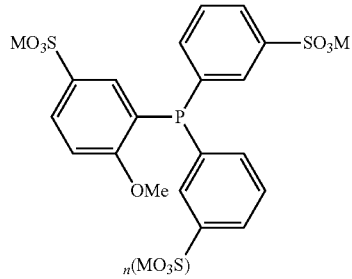

(I-6)
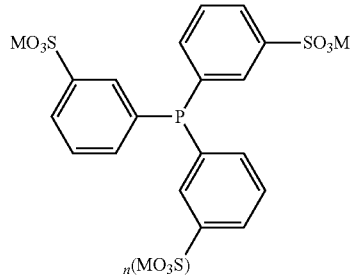

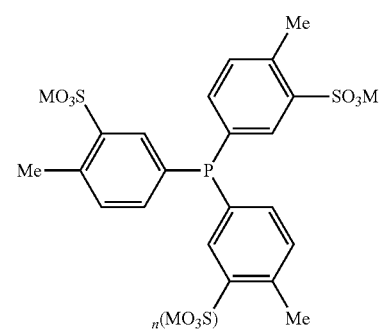 (I-7)
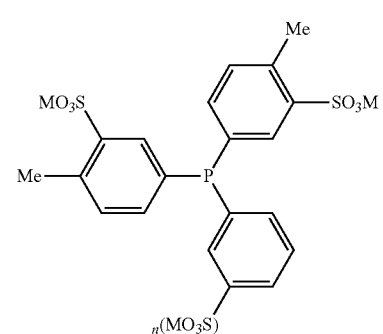 (I-8)
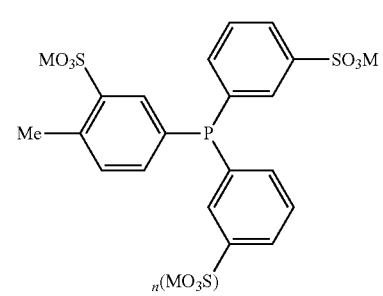 (I-9)
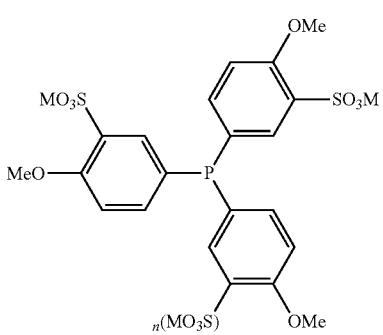 (I-10)
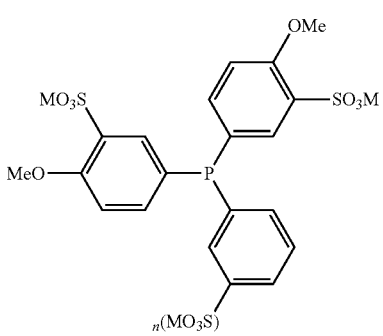 (I-11)
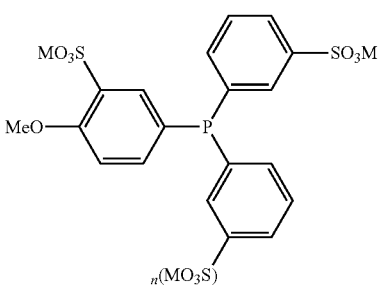 (I-12)
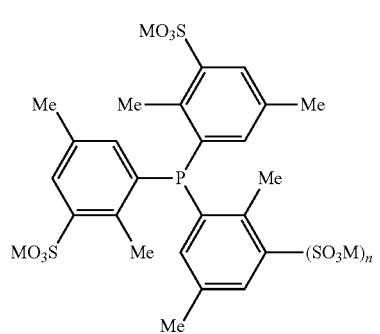 (I-13)
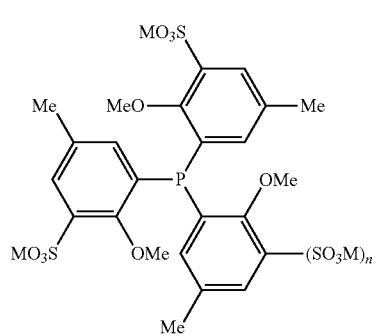 (I-14)
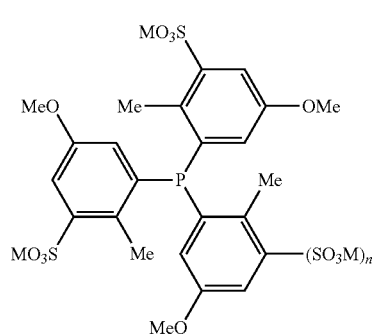 (I-15)

(I-16)
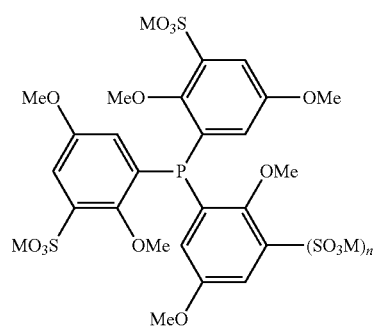
(I-17)
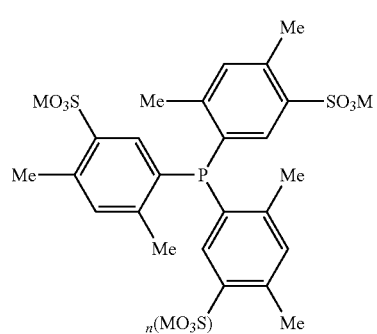
(I-18)
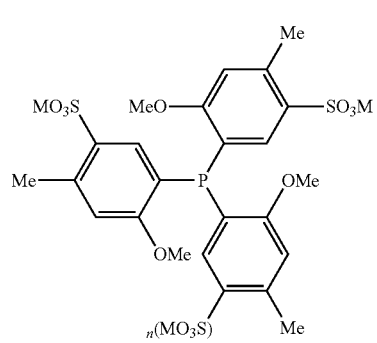
(I-19)
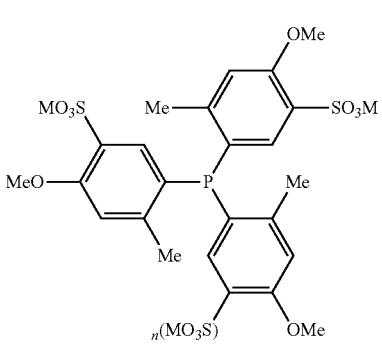
(I-20)
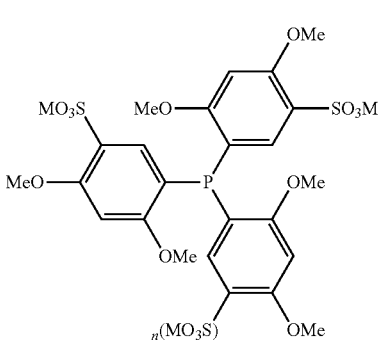
(I-21)
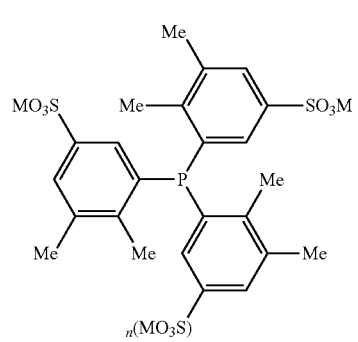
(I-22)
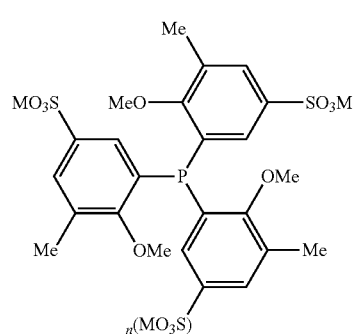
(I-23)
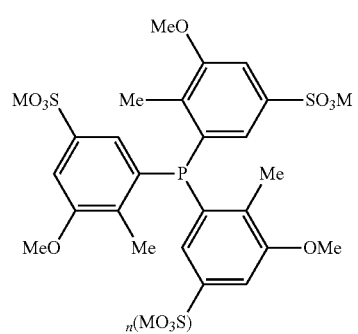
(I-24)
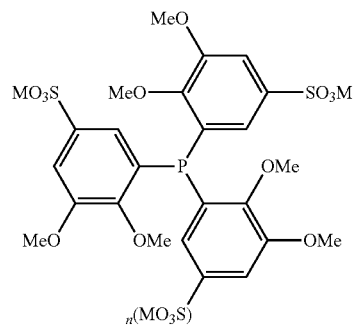

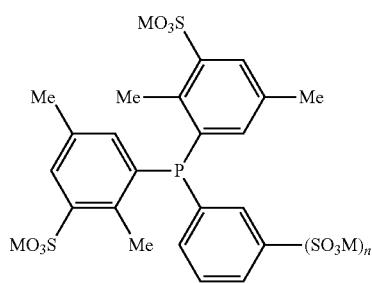
(I-25)
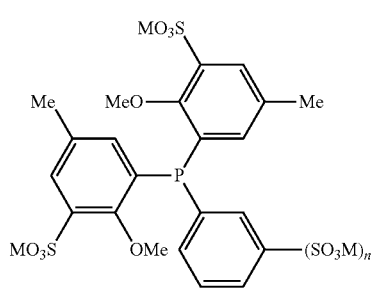
(I-26)
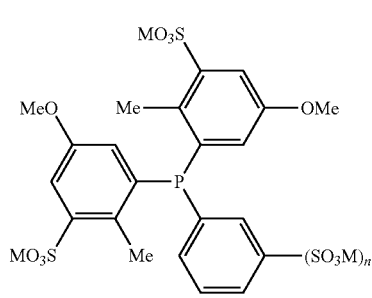
(I-27)
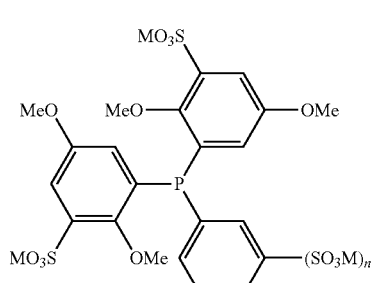
(I-28)
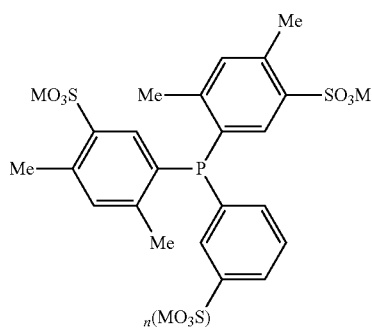
(I-29)
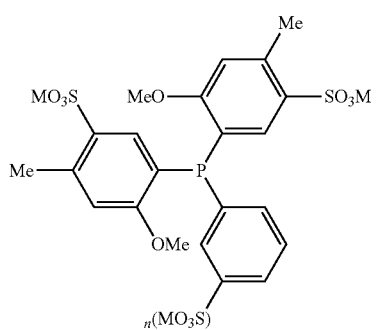
(I-30)
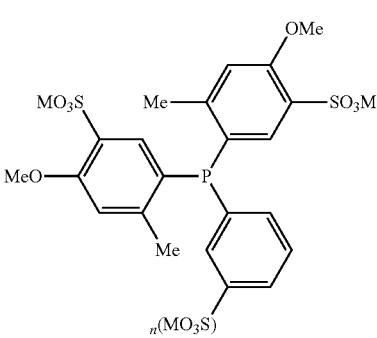
(I-31)
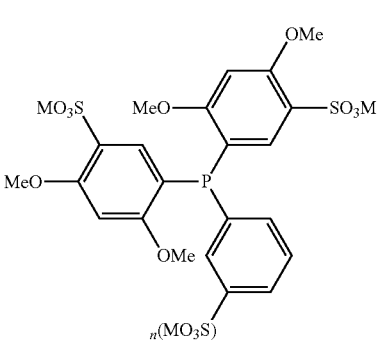
(I-32)
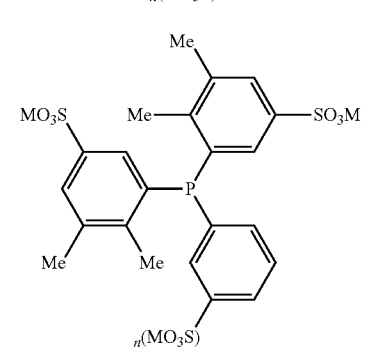
(I-33)
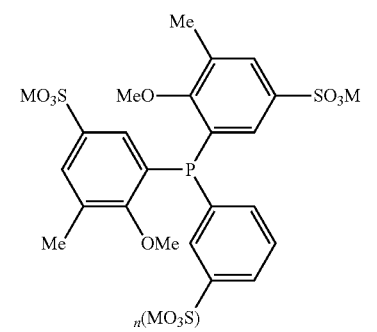
(I-34)

-continued

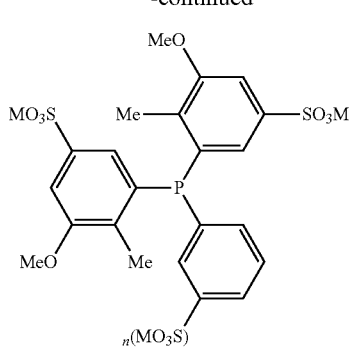

(I-35)

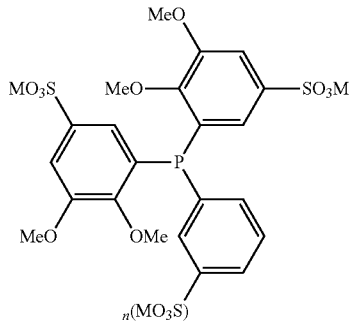

(I-36)

It is preferable to prepare a palladium catalyst for use in the production method of the present invention by dissolving the palladium compound and the water-soluble triarylphosphine in a solvent. As the solvent, the same kind of solvent as that for use in the telomerization may be used, and from the viewpoint of reduction in the amount of a solvent used, it is preferable to use water having the same purity as that for use in the telomerization as a solvent for dissolution of water-soluble triarylphosphine.

The water-soluble triarylphosphine for use in the present invention, in which a counter cation of a sulfonate group is a cation of a metal atom belonging to Group 1, can be produced by dissolving a triarylphosphine in sulfuric acid, followed by reacting it with fuming sulfuric acid as sulfuric acid containing sulfur trioxide (see, for example, Tetrahedron Letters, 2000, vol. 41, pp. 4503 to 4505; and Organic Process Research & Development, 2000, vol. 4, pp. 342 to 345).

In addition, the following methods are known.

A method of sulfonating triarylphosphine using an anhydrous mixture of sulfuric acid and orthoboric acid as a sulfonating agent (see, for example, JP-A-H08-176167).

A method of reacting triarylphosphine in which an electron donating group such as a methyl group or a methoxy group is introduced into an aromatic ring having a sulfonate group introduced in advance with sulfur trioxide in the presence of sulfuric acid (see, for example, Tetrahedron Letters, vol. 43, 2002, pp. 2543 to 2546).

A method of reacting triarylphosphine in which the same electron donating group such as a methyl group and a methoxy group are introduced into three aromatic rings with sulfur trioxide in the presence of sulfuric acid (see, for example, Advanced Synthesis & Catalysis, 2008, vol. 350, pp. 609 to 618).

A method of reacting an allylphosphide anion with halogenated allylsulfonate (see, for example, Chemical Reviews, 2009, vol. 109, no. 2, pp. 643 to 710).

The water-soluble triarylphosphine for use in the present invention, in which a counter cation of a sulfonate group is an ammonium cation derived from a tertiary amine, can be produced by reacting one in which the counter cation is a cation of a metal atom belonging to Group 1 with a tertiary amine in the presence of carbon dioxide and water (see JP-A-2003-171388). Further, the water-soluble triarylphosphine can be produced by reacting one in which a counter cation of a sulfonate group is an alkali metal ion with a protonic acid in a solvent such as a non-cyclic ketone, followed by neutralizing it with a tertiary amine (see JP-A-2002-371088). Further, the water-soluble triarylphosphine can be produced by dissolving one in which a counter cation of a sulfonate group is an alkali metal ion in a suitable solvent such as water and an alcohol, passing it through an acid anion-exchange resin bed, and then neutralizing it with a corresponding tertiary amine base (see JP-A-S63-88150).

In the sulfonation of a triarylphosphine, it is known to acquire a mixture of a mono-form, in which the number of sulfonate groups finally introduced is 1, a di-form, in which the number of sulfonate groups finally introduced is 2, and a tri-form, in which the number of sulfonate groups finally introduced is 3.

Based on the findings of the present inventors, as shown in Examples and Comparative Examples, the recovery of the palladium catalyst is very low in the mono-form, while it is high in the di-form and the tri-form. Accordingly, it is preferable to use a sulfonated triarylphosphine having a high content of the di-form and the tri-form as the water-soluble triarylphosphine in the present invention.

In the sulfonated triarylphosphine which is suitably used as the water-soluble triarylphosphine in the present invention, the total content of the di-form and the tri-form is preferably 80% by mole or more, and more preferably 90% by mole or more.

The sulfonated triarylphosphine with such a content of the di-form and the tri-form can be acquired by recrytallization of a mixture including a mono-form, a di-form, and a tri-form, by washing an aqueous solution of a mixture including the mono-form, the di-form, and the tri-form with a ketone-based solvent such as 2-butanone, and the like, or by performing column chromatography or the like.

(Solvent)

Usually, it is preferable to prepare a palladium catalyst from a palladium compound and a water-soluble triarylphosphine, using the production method of the present invention in the presence of a solvent in which the palladium compound is dissolved. It can be said that as the solvent in which the palladium compound is dissolved, a tertiary amine, an organic solvent having a dielectric constant of 2 to 18 at 25° C., or 2,7-octadien-1-ol generated by a telomerization can be used. The solvents may be used singly or as a mixture of two or more kinds thereof.

As the tertiary amine, a tertiary amine for use in a telomerization is preferably used, and that is, examples thereof include a tertiary amine, in which the total number of carbon atoms of a group bonded to one atom of nitrogen is 3 to 27. Specific examples thereof include trimethylamine, triethylamine, tripropylamine, triisopropylamine, tributylamine, triisobutylamine, tri-s-butylamine, tri-t-butylamine, tripentylamine, triisopentylamine, trineopentylamine, trihexylamine, triheptylamine, trioctylamine, triphenylamine, tribenzylamine, N,N-dimethylethylamine, N,N-dimethylpropylamine, N,N-dimethylisopropylamine, N,N-dimethylbutylamine, N,N-dimethylisobutylamine, N,N-dimethyl-s-butylamine, N,N-dimethyl-t-butylamine, N,N-dimethylpentylamine, N,N-dimethylisopentylamine, N,N- dimethylneopentylamine, N,N-dimethylhexylamine, N,N-dimethylheptylamine, N,N-dimethyloctylamine, N,N-dimethylnonylamine, N,N-dimethyldecylamine, N,N-dimethylundecylamine, N,N-dimethyldodecylamine, N,N-dimethylphenylamine, N,N-dimethylbenzylamine, N,N-diethylmonomethylamine, N,N-dipropylmonomethylamine, N,N-diisopropylmonomethylamine, N,N-dibutylmonomethylamine, N,N-diisobutylmonomethylamine, N,N-di-s-butylmonomethylamine, N,N-di-t-butylmonomethylamine, N,N-dipentylmonomethylamine, N,N-diisopentylmonomethylamine, N,N-dineopentylmonomethylamine, N,N-dihexylmonomethylamine, N,N-diheptylmonomethylamine, N,N-dioctylmonomethylamine, N,N-dinonylmonomethylamine, N,N-didecylmonomethylamine, N,N-diundecylmonomethylamine, N,N-didodecylmonomethylamine, N,N-diphenylmonomethylamine, N,N-dibenzylmonomethylamine, N,N-dipropylmonomethylamine, N,N-diisopropylmonoethylamine, N,N-dibutylmonoethylamine, N,N-diisobutylmonoethylamine, N,N-di-s-butylmonoethylamine, N,N-di-t-butylmonoethylamine, N,N-dipentylmonoethylamine, N,N-diisopentylmonoethylamine, N,N-dineopentylmonoethylamine, N,N-dihexylmonoethylamine, N,N-diheptylmonoethylamine, N,N-dioctylmonoethylamine, N,N-dinonylmonoethylamine, N,N-didecylmonoethylamine, N,N-diundecylmonoethylamine, N,N-didodecylmonoethylamine, N,N-diphenylmonoethylamine, and N,N-dibenzylmonoethylamine.

As the tertiary amine, a tertiary amine, in which the total number of carbon atoms of a group bonded to one atom of nitrogen is 3 to 24, is preferred, a tertiary amine, in which the total number of carbon atoms of a group bonded to one atom of nitrogen is 5 to 24, is more preferred, a tertiary amine, in which the total number of carbon atoms of a group bonded to one atom of nitrogen is 5 to 10, is still more preferred, and a tertiary amine, in which the total number of carbon atoms of a group bonded to one atom of nitrogen is 5 to 7, is particularly preferred. In particular, triethylamine, N,N-dimethylisopropylamine, and trioctylamine are preferred.

Furthermore, as an organic solvent having a dielectric constant of 2 to 18 at 25° C., one which is hardly consumed by the telomerization, and further, is the same as a solvent for recovering a palladium catalyst is preferably used from the viewpoint of simplification of solvent recovery and the like. Examples of such an organic solvent having a dielectric constant of 2 to 18 at 25° C. include n-dodecane, cyclohexane, 1,4-dioxane, benzene, p-xylene, m-xylene, toluene, dibutyl ether, diisopropyl ether, propanenitrile, ethylphenyl ether, diethyl ether, methyl-t-butyl ether, cyclopentyl methyl ether, fluorobenzene, 2-methyltetrahydrofuran, tetrahydrofuran, 2-heptanone, 4-methyl-2-pentanone, cyclopentanone, 2-hexanone, 2-pentanone, cyclohexanone, 3-pentanone, and acetophenone.

From the viewpoints of the recovery of the palladium catalyst and the easy availability, diethyl ether, diisopropyl ether, 2-methyltetrahydrofuran, tetrahydrofuran, or the like is preferably used.

It is possible to prepare a palladium catalyst from a palladium compound and a water-soluble triarylphosphine, but a method for producing the palladium catalyst varies depending on the valence of palladium contained in the palladium compound.

(i) Case of Using 0-Valent Palladium Compound

It is possible to prepare a palladium catalyst by reacting a 0-valent palladium compound with a water-soluble triarylphosphine in a solvent out of a telomerization system. On the other hand, it is also possible to prepare a palladium catalyst in a telomerization system by supplying a 0-valent palladium compound with a water-soluble triarylphosphine to the reaction system.

However, in a case of preparing it in the reaction system, there is a concern that the coordination of the water-soluble triarylphosphine with respect to the 0-valent palladium compound is impaired by a coordinating compound such as butadiene, and thus, the reaction is performed in a state in which a desired palladium catalyst active species cannot be sufficiently formed. Therefore, in a case of using the 0-valent palladium compound, it is preferable that a palladium catalyst is prepared from a 0-valent palladium compound and a water-soluble triarylphosphine out of a telomerization system.

(ii) Case of Using Divalent Palladium Compound

In a case of using a divalent palladium compound, it is necessary to produce a 0-valent palladium by reduction. It is also possible to prepare a palladium catalyst by reducing a divalent palladium compound out of a telomerization system, and reacting it with water-soluble triarylphosphine. On the other hand, it is also possible to prepare a palladium catalyst in the telomerization system by supplying a divalent palladium compound, a reducing agent, and a water-soluble triarylphosphine to the reaction system.

However, in a case of making an attempt to reducing the divalent palladium compound in the reaction system, there is a concern that since the concentrations of the divalent palladium compound and the reducing agent in the reaction system are low, it takes a long time to produce the palladium catalyst, and since the coordination of the water-soluble triarylphosphine with respect to the produced 0-valent palladium is impaired by a coordinating compound such as butadiene, the reaction is performed in a state in which a desired palladium catalyst active species cannot be sufficiently formed. Therefore, in a case of using the divalent palladium compound, it is preferable that a palladium catalyst is prepared by reacting a divalent palladium compound, a reducing agent, and a water-soluble triarylphosphine out of a telomerization system.

Furthermore, examples of the reducing agent which can be used for the reduction of divalent palladium include a phosphine compound, an alkali metal hydroxide, an alkali metal carboxylate, sodium borohydride, zinc powder, magnesium, and hydrazine. In view of operational convenience, it is preferable to use a phosphine compound, and it is more preferable to use a water-soluble triarylphosphine as a component constituting the palladium catalyst. A method for reducing such the divalent palladium compound by a phosphine compound is described in, for example, Journal of Organic Chemistry, 1995, no. 60, pp. 6829 to 6839; and Organometallics, 1993, vol. 12, pp. 1890 to 1901.

More specifically, the palladium catalyst is prepared by preparing a "divalent palladium compound solution" in which a divalent palladium compound such as palladium acetate (II) and bis(acetylacetone)palladium (II) is dissolved in a solvent selected from a tertiary amine being the same as one used for the telomerization, a solvent used for recovery of the palladium catalyst in the production method of the present invention having a dielectric constant of 2 to 18 at 25° C., and 2,7-octadien-1-ol produced by the telomerization, while preparing an aqueous solution of an water-soluble triarylphosphine, and sufficiently stirring the divalent palladium compound solution and the water-soluble triarylphosphine aqueous solution in a complete mixing tank.

Although not being particularly limited, it is preferable to prepare a palladium catalyst in a batch mode. Further, in a case where the prepared liquid is subjected to phase separation, the liquid may be supplied to the reaction system while sufficiently stirring, and the aqueous phase that has undergone phase separation may be supplied to the reaction system.

Preparation of the palladium catalyst is preferably carried out under light shielding in order to inhibit the produced palladium catalyst from being deformed.

Preparation of the palladium catalyst can be carried out in an atmosphere of nitrogen, argon, or helium as an inert gas, can be carried out in an atmosphere of carbon dioxide as an acidic gas or in an atmosphere of hydrogen as a reductive gas. Usually, from the viewpoint of operational convenience, it is preferable to prepare the palladium catalyst in an inert gas atmosphere, and it is more preferable to prepare the palladium catalyst in a nitrogen atmosphere from the viewpoint of low cost.

The content of palladium contained in 1 kg of a palladium catalyst liquid is preferably in the range of 0.001 moles to 1 mole in terms of palladium atoms. If the content is 0.001 moles or more, the time taken for the palladium catalyst to be formed gets shorter. Further, if the content is 1 mole or less, the palladium compound is sufficiently dissolved, and accordingly, the palladium catalyst is sufficiently formed.

The amount of the water-soluble triarylphosphine used per mole of palladium atom is preferably in the range of 2 moles to 100 moles, more preferably in the range of 2 moles to 40 moles, and still more preferably in the range of 2 moles to 15 moles. If the amount is 2 moles or more, the palladium catalyst is sufficiently formed. As a result, the selectivity for 2,7-octadien-1-ol is increased, in the recovery operation, the recovery is increased since formation of a palladium complex having high water solubility, coordinated with 2 moles or more of water-soluble triarylphosphine per atom of palladium is promoted. Further, if the amount is 100 moles or less, there is no concern that that reaction rate is decreased.

The temperature for preparation of the palladium catalyst is preferably in the range of 5° C. to 100° C., and more preferably in the range of 10° C. to 35° C. If the temperature is 5° C. or higher, time is not taken for formation of the 0-valent palladium catalyst, and if the temperature is 100° C. or lower, it is evitable that the 0-valent palladium catalyst is thermally instable, and thus, precipitation of the metal palladium can be inhibited.

The reaction time between the palladium compound and the water-soluble triarylphosphine is not particularly limited, but it is preferably in the range of 10 minutes to 240 minutes, and more preferably in the range of 30 minutes to 120 minutes. If the reaction time is 10 minutes or more, the 0-valent palladium catalyst is sufficiently formed. In addition, if the reaction time is greater than 240 minutes, there is no longer a change in formation of the palladium catalyst, leading to a limit.

[2. Telomerization Step]

The present step is a step of obtaining a telomerization solution containing 2,7-octadien-1-ol by subjecting butadiene and water to a telomerization in the presence of a palladium catalyst, a tertiary amine, and carbon dioxide.

The reaction can be carried out using a continuous stirred tank reactor, in any mode selected from two kinds of a batch (semi-continuous) mode and a flow and continuous mode. Depending on the cases, the reaction can be carried out in the flow and continuous mode by connecting two or three continuous stirred tank reactors in series. Particularly, from the viewpoint of employing suitable effects that 2,7-octadien-1-ol generated by the reaction promotes the mixing of water and butadiene, it is preferable to carry out the reaction in a flow and continuous mode, using a continuous stirred tank reactor. Further, the complete mixing type reactor as mentioned herein is a reactor designed such that raw materials supplied to a reactor are mixed while not leaving a moment in a substantially homogeneous dispersion state.

The amount of the palladium catalyst used is not particularly limited, but it is preferably in the range of 0.001 mmoles to 100 mmoles, and more preferably in the range of 0.01 mmoles to 10 mmoles, in terms of palladium atom per mole of butadiene. If the amount is 0.001 mmoles or more, the reaction rate is high and thus the reaction times is shorter, which is economically preferable. On the other hand, the amount may be more than 100 mmoles, but it causes the amount of the palladium catalyst used to be too high, and thus, there is a concern of economically bad effects as long as the amount does not cause the recovery of the palladium catalyst to be too high.

The amount of the water-soluble triarylphosphine present in the reaction system is not particularly limited, but the ratio thereof to the palladium atom in the step of preparing the palladium catalyst can be referenced, and specifically, the amount is preferably in the range of 2 moles to 100 moles, more preferably in the range of 2 moles to 40 moles, and still more preferably in the range of 2 moles to 15 moles, with respect to one mole of the palladium atom. In the present telomerization step, in a case of introducing additional water-soluble triarylphosphine, it is preferable to adjust the amount to be in this range. If the amount is 2 moles or more, the palladium catalyst is sufficiently formed, the side reaction by vinylcyclohexene or the like can be inhibited, and also, the reduction in the yield of 2,7-octadien-1-ol and the reduction in the recovery of the palladium catalyst can also be inhibited. On the other hand, if the amount is 100 moles or less, the coordination of the butadiene with respect to the palladium catalyst is not impaired and the reaction rate can be maintained.

In the telomerization system, the water-soluble triarylphosphine coexists with a tertiary amine, carbon dioxide, and water. Accordingly, as described in JP-A-2003-171388 or the like, M in a sulfonate group ($—SO_3M$), which is originally contained in the water-soluble triarylphosphine, may be an ammonium cation derived from the tertiary amine used in the reaction. Further, the sulfonate group ($—SO_3M$) may be ionized to $—SO_3—$ and $M^+$.

Furthermore, in the telomerization system, the water-soluble triarylphosphine coexists with an alkenyl compound such as 2,7-octadien-1-ol, which is a product. Accordingly, as described in JP-A-2002-371089 or the like, the water-soluble triarylphosphine may be reacted with 2,7-octadien-1-ol or the like to form a phosphonium salt.

As the water for use in the telomerization, pure water to an extent that does not adversely affect the telomerization is preferably used. For example, industrially, it is preferable to use ion exchange water or drain water obtained by aggregating steam. Further, in a case of including iron rust, since the water-soluble triarylphosphine is combined with a metal ion derived therefrom to form a complex, the palladium catalyst is insufficiently formed, and the side reaction to vinylcyclohexene or the like occurs. As a result, the yield of the 2,7-octadien-1-ol is reduced and the recovery of the palladium catalyst is reduced.

As the butadiene, any of hydrocarbon mixtures which are industrially available and commonly referred to a C4 fraction in petrochemistry can be used. However, since the palladium catalyst is poisoned by acetylene, sulfur, halogen, or the like, butadiene having a content of these components of 0.1 ppm or less is preferably used. Such the butadiene is referred to a polymerization grade product or a chemical reaction grade product, and is industrially available.

In the flow and continuous mode using a continuous stirred tank reactor, the range of mass ratio of butadiene and 2,7-octadien-1-ol present in the reaction system is not particularly limited by suitably setting the mass ratio depending on a desired butadiene conversion.

The mass ratio of butadiene and 2,7-octadien-1-ol present in the reaction system to water [(butadiene+2,7-octadien-1-ol)/water] is preferably 0.1 to 50, and more preferably 0.5 to 10. If this mass ratio is 0.1 or more, it is not necessary to increase the concentration of the palladium catalyst in the reaction system in order to achieve the industrially satisfactory productivity of 2,7-octadien-1-ol. On the other hand, if the mass ratio is 50 or less, it is easy to acquire aqueous phase even while not newly adding water at a time of recovery of the palladium catalyst.

The tertiary amine which is used in the telomerization is reacted with water and carbon dioxide in the reaction system, thereby generating ammonium ions and hydrogen carbonate ions. The reaction intermediates formed from one atom of palladium, one molecule of a water-soluble triarylphosphine, 2 molecules of butadiene, and the like are attacked by hydrogen carbonate ions, thereby producing 2,7-octadien-1-ol.

Examples of the tertiary amine include a tertiary amine, in which the total number of carbon atoms of a group bonded to one atom of nitrogen is 3 to 27, and specific examples thereof include trimethylamine, triethylamine, tripropylamine, triisopropylamine, tributylamine, triisobutylamine, tri-s-butylamine, tri-t-butylamine, tripentylamine, triisopentylamine, trineopentylamine, trihexylamine, triheptylamine, trioctylamine, trinonylamine, tridecylamine, triundecylamine, tridodecylamine, triphenylamine, tribenzylamine, N,N-dimethylethylamine, N,N-dimethylprop ylamine, N,N-dimethylisopropylamine, N,N-dimethylbutylamine, N,N-dimethylisobutylamine, N,N-dimethyl-s-butylamine, N,N-dimethyl-t-butylamine, N,N-dimethylpentylamine, N,N-dimethylisopentylamine, N,N-dimethylneopentylamine, N,N-dimethylhexylamine, N,N-dimethylheptylamine, N,N-dimethyloctylamine, N,N-dimethylnonylamine, N,N-dimethyldecylamine, N,N-dimethylundecylamine, N,N-dimethyldodecylamine, N,N-dimethylphenylamine, N,N-dimethylbenzylamine, N,N-diethylmonomethylamine, N,N-dipropylmonomethylamine, N,N-diisopropylmonomethylamine, N,N-dibutylmonomethylamine, N,N-diisobutylmonomethylamine, N,N-di-s-butylmonomethylamine, N,N-di-t-butylmonomethylamine, N,N-dipentylmonomethylamine, N,N-diisopentylmonomethylamine, N,N-dineopentylmonomethylamine, N,N-dihexylmonomethylamine, N,N-diheptylmonomethylamine, N,N-dioctylmonomethylamine, N,N-dinonylmonomethylamine, N,N-didecylmonomethylamine, N,N-diundecylmonomethylamine, N,N-didodecylmonomethylamine, N,N-diphenylmonomethylamine, N,N-dibenzylmonomethylamine, N,N-dipropylmonomethylamine, N,N-diisopropylmonoethylamine, N,N-dibutylmonoethylamine, N,N-diisobutylmonoethylamine, N,N-di-s-butylmonoethylamine, N,N-di-t-butylmonoethylamine, N,N-dipentylmonoethylamine, N,N-diisopentylmonoethylamine, N,N-dineopentylmonoethylamine, N,N-dihexylmonoethylamine, N,N-diheptylmonoethylamine, N,N-dioctylmonoethylamine, N,N-dinonylmonoethylamine, N,N-didecylmonoethylamine, N,N-diundecylmonoethylamine, N,N-didodecylmonoethylamine, N,N-diphenylmonoethylamine, and N,N-dibenzylmonoethylamine.

According to the investigations conducted by the present inventors, it was demonstrated that in a case of using a tertiary amine, in which the total number of carbon atoms of a group bonded to one atom of nitrogen is 5 to 7, it can be expected that the recovery of the palladium catalyst is further improved, as compared with a case of using a trimethylamine, in which the total number of carbon atoms of a group bonded to one atom of nitrogen is 3, or a case of using N,N-dimethylethylamine, in which the total number of carbon atoms of a group bonded to one atom of nitrogen is 4. That is, as a tertiary amine capable of improving the reaction rate and the selectivity for 2,7-octadien-1-ol with a small amount of the tertiary amine used, as well as accomplishing a good recovery of the palladium catalyst, those in which the total number of carbon atoms of a group bonded to one atom of nitrogen is 5 to 7 are preferred, and among these, from the viewpoint of industrially easy availability or the like, triethylamine and N,N-dimethylisopropylamine are more preferred.

The mass ratio of the tertiary amine to water [tertiary amine/water] is preferably 0.1 to 10, and more preferably 0.5 to 5. If the mass ratio is 0.1 or more, the hydrogen carbonate ion concentration in the reaction system is sufficiently increased, and correspondingly, the reaction rate is increased, whereby it is possible to inhibit 1,3,7-octatriene and vinylcyclohexene from being by-produced. Further, if the mass ratio is 10.0 or less, there is no concern that the coordination of the water-soluble triarylphosphine with respect to 0-valent palladium is impaired, and as a result, 1,3,7-octatriene and vinylcyclohexene can be inhibited from being by-produced.

The telomerization may be carried out in the presence of a solvent. As the solvent, a solvent which is less likely to be consumed by the telomerization and is the same as a solvent for recovery of a palladium catalyst is preferred, from the viewpoint of simplification of solvent recovery or the like. Examples of the solvent include ethers such as 1,4-dioxane, dibutyl ether, diisopropyl ether, ethylphenyl ether, diethyl ether, methylethyl ether, dimethyl ether, methyl-t-butyl ether, cyclopentylmethyl ether, 2-methyltetrahydrofuran, 3-methyltetrahydrofuran, tetrahydrofuran, ethylene glycol dimethyl ether, tetraethylene glycol dimethyl ether, and methylisopropyl ether; ketones such as 2-heptanone, 4-methyl-2-pentanone, cyclopentanone, 2-hexanone, 2-pentanone, cyclohexanone, 3-pentanone, acetophenone, 2-butanone, and acetone; nitriles such as propanenitrile, benzonitrile, and acetonitrile; aromatic hydrocarbons such as benzene, p-xylene, m-xylene, toluene, fluorobenzene, and ethylbenzene; alkanes such as n-dodecane, cyclohexane, n-pentane, n-hexane, and n-heptane; alkenes such as 1-hexene and 1-octene; sulfoxides such as dimethylsulfoxide; pyridine derivatives such as pyridine and α-picoline; and amides such as acetamide, propionamide, N,N-dimethylformamide, and N,N-dimethylacetamide. Among these, preferred are solvents having a dielectric constant of 2 to 18 at 25° C., such as 1,4-dioxane, dibutyl ether, diisopropyl ether, ethylphenyl ether, diethyl ether, methyl-t-butyl ether, cyclopentylmethyl ether, 2-methyltetrahydrofuran, tetrahydrofuran, 2-heptanone, 4-methyl-2-pentanone, cyclopentanone, 2-hexanone, 2-pentanone, cyclohexanone, 3-pentanone, acetophenone, propanenitrile, benzene, p-xylene, m-xylene, toluene, fluorobenzene, n-dodecane, and cyclohexane.

In a case of using the solvent, the amount of the solvent used is not particularly limited, but from the viewpoint of inhibiting the palladium catalyst from migrating to the aqueous phase to maintain a high reaction rate, the mass ratio thereof to water [solvent/water] is preferably 2.0 or less, and it is preferable that the solvent out of the palladium catalyst solution is not put into the telomerization system. Further, since the butadiene and the tertiary amine used in the telomerization, and 2,7-octadien-1-ol of the product are used as an alternative to the solvent, the telomerization can be efficiently carried out even without further addition of the solvent.

The telomerization temperature is preferably 130° C. or lower, and preferably 50° C. to 100° C. If the telomerization temperature is 130° C. or lower, it is possible to inhibit high-boiling products (hereinafter referred to as high boiling substances), thereby maintaining a high yield of 2,7-octadien-1-ol. In addition, if the telomerization temperature is 50° C. or higher, the activity of the palladium catalyst is not lowered, and it is not necessary to increase the concentration of the palladium catalyst.

The amount of carbon dioxide introduced is preferably adjusted such that the total pressure in the reaction system after carbon dioxide has been introduced into the reaction system is 0.5 MPa (the pressure described in the present specification is a value of a gauge pressure, which shall apply hereinafter) or more, and is more preferably adjusted such that the total pressure is 0.5 MPa to 3.0 MPa. If the total pressure in the reaction system after carbon dioxide has been introduced into the reaction system is 0.5 MPa or more, the reaction rate is increased since the hydrogen carbonate ion concentration in the reaction system is sufficiently high, and further, it is possible to inhibit by-production of 1,3,7-octatriene and vinylcyclohexene. Further, the total pressure in the reaction system after carbon dioxide has been introduced into the reaction system may also be more than 3.0 MPa, but in such a case, there is no usually improvement in the selectivity for 2,7-octadien-1-ol and further facilities such as a reactor that withstands high pressure and a compressor for supply of carbon dioxide are required, and therefore, there is no specific economic advantage.

[3. Catalyst Recovering Step and Product Separating Step]

In the present step, the telomerization solution obtained by the telomerization is mixed with an organic solvent having a dielectric constant at of 2 to 18 25° C., followed by carrying out phase separation in the presence of carbon dioxide, and then 2,7-octadien-1-ol is obtained from the organic phase (product separating step), while recovering an aqueous phase including a palladium catalyst (catalyst recovering step).

In addition, when carrying out the present step, a part of butadiene and carbon dioxide may be removed in advance from the telomerization solution, if necessary.

(Catalyst Recovering Step)

The recovery and reuse of the palladium catalyst after mixing the telomerization solution with an organic solvent having a dielectric constant of 2 to 18 at 25° C., and then carrying out phase separation in the presence of carbon dioxide, can be carried out in the following manner, for example.

The aqueous phase obtained by carrying out phase separation can be supplied to the telomerization as it is or as appropriately concentrated or diluted [first round in catalyst recovery]. On the other hand, the organic phase obtained by carrying out phase separation was mixed with at least one selected from water and a tertiary amine, followed by carrying out phase separation in the presence of carbon dioxide, as necessary. The obtained aqueous phase is supplied to the telomerization as it is or as appropriately concentrated or diluted [second round in catalyst recovery]. The second round in the catalyst recovery operation may be repeated. At least the first round in the catalyst recovery operation is carried out in the presence of carbon dioxide, but the second round in the catalyst recovery operation may be carried out in the presence or absence of carbon dioxide. Further, there are some cases where a tertiary amine is added for the purpose of increasing the recovery of the palladium catalyst.

For the recovery of the palladium catalyst, a stirring type extractor, a rotating disc (RDC) type extractor, a perforated plate, or the like, which is for an industrially general purpose, can be used. Industrially, it is also possible to carry out a catalyst recovery operation in a continuous mode by providing a settler that is sufficient for carrying out phase separation. In addition, by linking these in series, the recovery of the palladium catalyst may be enhanced by multi-stage recovery.

In a case of carrying out phase separation at a higher carbon dioxide pressure than the total pressure during the telomerization, it takes time corresponding to dissolution of carbon dioxide in a telomerization solution and a solvent, and thus, a continuous mode is preferable from the viewpoint of an increase in the amount of carbon dioxide dissolved.

(First Round in Catalyst Recovery)

The present inventors have found that the kind of an organic solvent used for phase separation is important. For example, in a case of using n-hexane having a dielectric constant of 1.88, 2-butanone having a dielectric constant of 18.25, acetonitrile having a dielectric constant of 35.69, or the like, the recovery of the palladium catalyst is low, and with an organic solvent having a dielectric constant of 2 to 18, the recovery of the palladium catalyst is increased.

Although a detailed reason why such results are obtained is not clear, it is thought that in a case of using an organic solvent having a dielectric constant of more than 18, the aqueous phase is dissolved in the organic phase, and as a result, the recovery of the palladium catalyst is decreased. On the other hand, it is presumed that in a case of using an organic solvent having a dielectric constant of less than 2, carbon dioxide is less soluble in the organic phase, and as a result, the ionization state of the phosphonium salt formed by the reaction between the water-soluble triarylphosphines and 2,7-octadien-1-ol becomes insufficient, and thus, a lot of the palladium catalyst is present in the organic phase. It is presumed that in order to avoid these, it is suitable to use an organic solvent having a dielectric constant of 2 to 18.

The organic solvent having a dielectric constant of 2 to 18 at 25° C. is not particularly limited as long as it is not substantially reacted with butadiene, and examples thereof include n-dodecane having a dielectric constant of 2.01, cyclohexane having a dielectric constant of 2.02, 1,4-dioxane having a dielectric constant of 2.21, benzene having a dielectric constant of 2.27, p-xylene having a dielectric constant of 2.27, m-xylene having a dielectric constant of 2.35, toluene having a dielectric constant of 2.37, dibutyl ether having a dielectric constant of 3.05, diisopropyl ether having a dielectric constant of 3.38, propanenitrile having a dielectric constant of 3.44, ethyl phenyl ether having a dielectric constant of 4.18, diethyl ether having a dielectric constant of 4.24, methyl-t-butyl ether having a dielectric constant of 4.50, cyclopentylmethyl ether having a dielectric constant of 4.76, fluorobenzene having a dielectric constant of 5.42, 2-methyltetrahydrofuran having a dielectric constant of 6.20, tetrahydrofuran having a dielectric constant of 7.43, 2-heptanone having a dielectric constant of 11.66, 4-methyl-2-pentanone having a dielectric constant of 12.89, cyclopentanone having a dielectric constant of 13.58, 2-hexanone having a dielectric constant of 14.14, 2-pentanone having a dielectric constant of 15.20, cyclohexanone having a dielectric constant of 15.62, 3-pentanone having a dielectric constant of 16.78, and acetophenone having a dielectric constant of 17.44.

The dielectric constants in such organic solvents at 25° C. are summarized in Table 1 below.

TABLE 1

| Organic solvent | Dielectric constant | Organic solvent | Dielectric constant | Organic solvent | Dielectric constant |
|---|---|---|---|---|---|
| n-Dodecane | 2.01 | Dibutyl ether | 3.05 | 2-Heptanone | 11.66 |
| Cyclohexane | 2.02 | Diisopropyl ether | 3.38 | 4-Methyl-2-heptanone | 12.89 |
| 1,4-Dioxane | 2.21 | Propanenitrile | 3.44 | | |
| Benzene | 2.27 | Ethylphenyl ether | 4.18 | Cyclopentanone | 13.58 |
| p-Xylene | 2.27 | Diethyl ether | 4.24 | 2-Hexanone | 14.14 |
| m-Xylene | 2.35 | Methyl-t-butyl ether | 4.50 | 2-Pentanone | 15.20 |
| Toluene | 2.37 | Cyclopentylmethyl ether | 4.76 | Cyclohexanone | 15.62 |
| | | Fluorobenzene | 5.42 | 3-Pentanone | 16.78 |
| | | 2-Methyltetrahydrofuran | 6.20 | Acetophenone | 17.44 |
| | | Tetrahydrofuran | 7.43 | | |

Among those, it is more preferable to use an organic solvent having a dielectric constant of 3 to 10. Examples of the organic solvent having a dielectric constant of 3 to 10 include dibutyl ether, diisopropyl ether, propanenitrile, ethylphenyl ether, diethyl ether, methyl-t-butyl ether, cyclopentylmethyl ether, fluorobenzene, 2-methyltetrahydrofuran, and tetrahydrofuran.

These organic solvents having a dielectric constant of 2 to 18 may be used singly or as a mixture of two or more kinds thereof. Further, they may be mixed with an organic solvent other than a solvent having a dielectric constant of 2 to 18, which is not substantially reacted with butadiene and 2,7-octadien-1-ol, and then used. However, the amount of the organic solvent other than a solvent having a dielectric constant of 2 to 18 to be used is preferably 40 parts by mass or less, more preferably 20 parts by mass or less, and still more preferably 10 parts by mass or less, with respect to 100 parts by mass of the organic solvent having a dielectric constant of 2 to 18.

The mass ratio of the organic solvent having a dielectric constant of 2 to 18 to the telomerization solution [organic solvent having a dielectric constant of 2 to 18/telomerization solution] is preferably 0.25 to 5.0, and more preferably 0.5 to 2.5. If the present mass ratio is 0.25 or more, the recovery of the palladium catalyst is increased. On the other hand, the recovery of the palladium catalyst may be more than 5.0, but a remarkable enhancement in the recovery of the palladium catalyst is not confirmed, the amount of energy consumed at a time of separation by distillation with 2,7-octadien-1-ol required for recovery and reuse of an organic solvent having a dielectric constant of 2 to 18 is increased, and the scale of facilities for separation by distillation is increased.

During the recovery of the palladium catalyst, a tertiary amine may further be added. Examples of the tertiary amine include the same tertiary amines used for the telomerization above.

From the viewpoint of facilitating the recovery of the tertiary amine, it is preferable that the same kind of tertiary amine as those for the telomerization is used or a tertiary amine is not added.

It is also possible to increase the recovery of the palladium catalyst by adding water when the telomerization solution is mixed with an organic solvent having a dielectric constant of 2 to 18 at 25° C. However, in order to reuse the palladium catalyst in the telomerization system, it is preferable to add the aqueous phase including the palladium catalyst in an amount to an extent such that concentration is not required.

Furthermore, the temperature at a time of phase separation is preferably 5° C. to 90° C., and from the viewpoint that a lower temperature results in an increased phase separation rate, the temperature is more preferably 5° C. to 40° C.

The present inventors have found that an increased pressure of the carbon dioxide at a time of phase separation enhances the recovery of palladium catalyst.

When the phase separation is carried out in the presence of carbon dioxide, the total pressure is set to preferably 0.1 MPa or more, and more preferably to 0.2 MPa to 3 MPa. Even when the total pressure is more than 3 MPa, a significant change in the recovery of the palladium catalyst cannot be observed, and facilities such as a high-pressure corresponding extractor and a compressor for supplying carbon dioxide are required.

It is preferable that a saturated amount of carbon dioxide is dissolved in a mixed liquid in the reaction system after pressurization with carbon dioxide, but from the viewpoint that it takes time to reach a saturation state, in a case of a continuous mode, pressurization is carried out for a retention time of the mixed liquid in the reaction system, which is adjusted preferably to 0.1 hours to 10 hours, and more preferably to 0.2 hours to 5 hours. If the retention time is 0.1 hours or more, the amount of carbon dioxide dissolved becomes sufficient, and the recovery of the palladium catalyst with respect to the aqueous phase obtained by the phase separation is increased. On the other hand, the retention time may be more than 10 hours, but there is little effect of enhancing the recovery of the palladium catalyst due to an increase in the amount of carbon dioxide dissolved.

(Second and Subsequent Rounds in Catalyst Recovery)

By the first round in catalyst recovery above, it is possible to recover most of the palladium catalyst and the tertiary amine, but there are some cases where a part of the palladium catalyst remains in the separated organic phase. Therefore, it is preferable to further recover the palladium catalyst from the organic phase.

The amount of water added to the separated organic phase is adjusted such that the mass ratio of the organic phase to water [organic phase/water] is preferably 0.05 to 0.5, and more preferably 0.1 to 0.25. If the mass ratio is 0.05 or more, the time taken for phase separation is shortened, whereas if the mass ratio is 0.5 or more, the volume efficiency can be maintained high, and thus, reduction in economy. Further, the total amount of water used for catalyst recovery after the second round in catalyst recovery is preferably controlled to be no more than the amount of water consumed in the telomerization.

The tertiary amine may be appropriately added to the separated organic phase, and in this case, the amount of the tertiary amine added is one such that the mass ratio of the tertiary amine to the organic phase [tertiary amine/organic phase] is preferably 0.5 or less, and more preferably 0.25 or less. If the mass ratio is 0.5 or less, there is no concern that the volume efficiency becomes too low.

An organic solvent having a dielectric constant of 2 to 18 may further be added to the separated organic phase.

The phase separation temperature, the carbon dioxide pressure, and the like are preferably in the same ranges as in the conditions for the first round in catalyst recovery.

The total amount of water and the tertiary amine contained in the aqueous phase, which is acquired through the first round in catalyst recovery and the second and subsequent rounds in catalyst recovery, is preferably controlled by a means for, for example, suitable concentration of the aqueous phase including the acquired palladium catalyst so as to make it possible to continue a long-term stable operation industrially, while not changing the composition of the telomerization solution over time and not causing problems such as appropriate change in the distillation condition, when the aqueous phase is supplied to the telomerization system again and reused.

In a case where the aqueous phase including the palladium catalyst is concentrated, concentration is carried out at preferably 150° C. or lower, and more preferably 100° C. or lower. Further, at a time of concentration, an inert gas such as nitrogen, helium, and argon may coexist, if necessary, and carbon dioxide may coexist.

(Product Separating Step)

2,7-Octadien-1-ol, which is a desired product, is obtained from the organic phase obtained by carrying out phase separation.

The organic phase usually includes butadiene, a solvent having a dielectric constant 2 to 18, and 2,7-octadien-1-ol. Depending on cases, the organic phase includes carbon dioxide and a tertiary amine.

Carbon dioxide and butadiene are removed by flushing the organic phase, and at the same time, the removed carbon dioxide and butadiene are reused in the telomerization system, if necessary.

The respective components of the tertiary amine, the organic solvent having a dielectric constant of 2 to 18, 2,7-octadien-1-ol, and the like can be separated by distillation. The separated tertiary amine may be reused for the telomerization or catalyst recovery. Further, the separated organic solvent having a dielectric constant of 2 to 18 may be used for catalyst recovery.

A fraction mainly composed of 2,7-octadien-1-ol which is a desired product can be purified by vacuum distillation. The distillation temperature of the fraction mainly composed of 2,7-octadien-1-ol can be appropriately selected by the pressure in the distillation system, but in a case where the fraction is warmed up to around 200° C. in the presence of a trace amount of the palladium catalyst, the reaction for 1,3,7-octatriene of 2,7-octadien-1-ol, or the like proceeds, and therefore, the temperature is preferably 200° C. or lower, and more preferably 140° C. or lower.

EXAMPLES

Hereinafter, the present invention will be described in more detail with reference to Examples or the like, but the present invention is not limited to such Examples in any case.

Production of the water-soluble triarylphosphine for use in the present invention is carried out at room temperature, at normal pressure, or under a nitrogen atmosphere unless otherwise specified, and as the solvent, those which had been replaced with nitrogen in advance were used.

In addition, the water-soluble triarylphosphine obtained by sulfonating triaryl phosphine is a mixture of those in which the number of sulfonate groups introduced is 1 to 3, and further includes oxides formed by oxidization of such the phosphorus.

These composition ratios (mass ratios) in the water-soluble triarylphosphine are quantified from peak areas of $^{31}P$ obtained through measurement by subjecting a dimethylsulfoxide-$d_6$ (hereinafter referred to as DMSO-$d_6$) solution prepared such that the ratio of the produced water-soluble triarylphosphine is 0.05 mol/L to a nuclear magnetic resonance apparatus "AVANCEIII 400 USPlus" (manufactured by Bruker BioSpin K. K.). In this case, the chemical shift of $^{31}P$ is a value at 305 K in the case where the chemical shift of the DMSO-$d_6$ solution prepared such that the ratio of the phosphoric acid is 0.05 mol/L is set to 0 ppm.

Furthermore, sodium ions were quantified using an atomic absorption spectrophotometer "AA-7000 F" (manufactured by Shimadzu Corporation).

Production of Water-Soluble Triarylphosphine

Reference Example 1

A sulfonation reaction was carried out in a batch mode. A 50-L glass-lined reactor equipped with a thermometer, a stirring device, and a jacket was used. 9.84 kg of concentrated sulfuric acid at a concentration of 97.4% by weight was placed in the reactor and cooled to 16° C. under stirring. Subsequently, 10.91 kg (35.84 mol) of tris(2-methylphenyl)phosphine (hereinafter referred to as TOTP) was introduced thereinto for 1 hour so as to keep the temperature at 30° C. or lower. Thereafter, 37.60 kg (131.50 mol in terms of sulfur trioxide) of fuming sulfuric acid containing 28% by mass of sulfur trioxide was added thereto for 3 hours, while controlling the liquid temperature to a range of 30° C. to 40° C. Subsequently, the flow path of fuming sulfuric acid was washed with 1 kg of concentrated sulfuric acid at a concentration of 97.4% by weight. The reaction was carried out at a liquid temperature of 20° C. to 30° C. for 4 hours.

On the other hand, 70 kg of ion exchange water was placed in a 200-L glass-lined reactor equipped with a thermometer, a stirring device, and a jacket, and the total amount of the above sulfonation reaction solution was transferred thereto over 1 hour. Further, the flow path of the sulfonation reaction solution was washed with 10 kg of ion exchange water, and added to the above diluted liquid. In addition, the liquid temperature was controlled to a range of 20° C. to 40° C., thereby acquiring 137.80 kg of a diluted sulfonation reaction.

27.50 kg (7.15 mol in terms of phosphorous atoms) of a diluted sulfonated reaction solution and 5 kg of ion exchange water were added to a 200-L glass-lined reactor equipped with a thermometer, a stirring device, and a jacket. 24.10 kg of an aqueous sodium hydroxide solution at 30.2% by mass was supplied thereto for 3 hours while controlling the liquid temperature to a range of 10° C. to 30° C. Further, 1.66 kg of an aqueous sodium hydroxide solution at 4% by mass was added thereto for 1.7 hours. Thus, a neutralizing liquid at pH 7.99 was acquired.

The neutralizing liquid was allowed to exist in the range of 80 kPa to 100 kPa at 35° C. to 65° C. and concentrated for 4.5 hours, and 37 kg of water was evaporated therefrom. 45 kg of methanol was added to the concentrate, followed by stirring at 40° C. for 1 hour. Further, the mixture was allowed to exist in the range of 4 kPa to 55 kPa at 40° C. to 55° C. and concentrated for 2.4 hours, and 45 kg of methanol was evaporated therefrom. 147 kg of methanol was added to the concentrate, followed by stirring at 40° C. to 60° C. for 1 hour. Thereafter, the mixture was cooled to 30° C. or lower.

The methanol solution was allowed to pass through an SUS304-made pressure filter in which 5 kg of "Celpure (registered trademark) S1000" manufactured by Advanced Minerals Corporation, as a high-purity diatomite filter aid was placed, thereby acquiring a filtrate. In addition, the filter aid was washed with 28 kg of methanol and the filtrate was combined with the above filtrate.

The total amount of the above acquired methanol solution was put into a 100-L glass-lined reactor equipped with a thermometer, a stirring device, and a jacket, allowed to exist in the range of 4 kPa to 55 kPa at 40° C. to 55° C., and concentrated to dryness for 18 hours, thereby acquiring 3.56 kg of a white solid (hereinafter referred to as an acquisition 1).

The acquisition was a mixture including 0.13 kg (0.33 mol, 4.75% by mole) of a bis(2-methylphenyl)(6-methyl-3-sulfonatophenyl)phosphine sodium salt as a mono-form, 2.91 kg (5.72 mol, 82.99% by mole) of a bis(6-methyl-3-sulfonatophenyl)(2-methylphenyl)phosphine disodium salt as a di-form, and 0.52 kg (0.85 mol, 12.26% by mole) of a tris(6-methyl-3-sulfonatophenyl)phosphine trisodium salt as a tri-form. From the viewpoint that 3.56 kg (6.90 mol in terms of phosphorous atoms) of the acquisition 1 could be acquired from 27.50 kg (7.15 mol in terms of phosphorous atoms) of a diluted sulfonated reaction solution, the yield based on the phosphorous atoms ranging from the sulfonation step to the neutralization step was 96.5%.

An acrylic resin-made column (100 mm in diameter and 760 mm in height) filled with 5 kg of a strongly acidic cation exchange resin "Dowex G-26" was prepared. 12 kg of an aqueous solution including the acquisition 1 at 8.6% by mass (1044.0 g in terms of the acquisition 1, 2023.4 mmol in terms of phosphorous atoms) was allowed to pass through from the upper part of a column to a linear velocity of 9.3 m/hr to 12.5 m/hr. The obtained aqueous solution was concentrated to dryness in the range of 35° C. to 70° C. at 4 kPa to 55 kPa to obtain 914.5 g of a white solid (hereinafter referred to as an acquisition 2).

$^{31}$P-NMR (400 MHz, 305 K, DMSO-$d_6$, phosphoric acid, ppm) δ: a bis(2-methylphenyl)(6-methyl-3-sulfophenyl)phosphine as a mono-form showed a peak at −28.72, a bis(6-methyl-3-sulfophenyl)(2-methylphenyl)phosphine as a di-form showed a peak at −26.00, and a tris(6-methyl-3-sulfophenyl)phosphine as a tri-form showed a peak at −18.85.

The acquisition 2 was a mixture including 35.3 g (91.9 mmol, 4.73% by mole) of bis(2-methylphenyl)(6-methyl-3-sulfophenyl)phosphine, 749.4 g (1613.4 mmol, 83.01% by mole) of bis(6-methyl-3-sulfophenyl)(2-methylphenyl)phosphine, and 129.8 g (238.3 mmol, 12.26% by mole) of tris(6-methyl-3-sulfophenyl)phosphine According to the atomic absorption analysis of the acquisition 2, the sodium content included in the acquisition 2 was 23 ppm or less in terms of sodium atoms. From the viewpoint that the number of sulfo groups contained in 1.0 kg of the acquisition 2 was 4410.6 mmol and the content of the sodium atoms is 1.0 mmol, 99.98% by mole or more of the sulfonate groups could be converted into sulfo groups.

From the viewpoint that 914.5 g (1943.6 mmol in terms of phosphorous atoms) of an acquisition 2 could be acquired using 1044.0 kg (2023.4 mmol in terms of phosphorous atoms) of the acquisition 1, the yield based on the phosphorous atoms in the ion exchange step was 95.5%.

500 g of an aqueous solution including 10% by mass of the acquisition 2 was prepared. Further, this aqueous solution includes 50.0 g of the acquisition 2 with 106.3 mmol in terms of phosphorous atoms and 221.4 mmol of sulfo groups. By placing an aqueous solution of the acquisition 2 in a 3-neck flask having an inner capacity of 1 L, equipped with a thermometer, a stirring device, a dropping funnel, and a nitrogen gas line, 24.6 g (243.5 mmol) of triethylamine was added thereto through the dropping funnel, followed by stirring in the range of 20° C. to 30° C. for 1 hour to perform a reaction.

Thereafter, the reaction solution was concentrated to dryness in the range of 35° C. to 70° C. and 4 kPa to 56 kPa, thereby acquiring 68.2 g of a white solid (hereinafter referred to as an acquisition 3).

$^{31}$P-NMR (400 MHz, 305 K, DMSO-$d_6$, phosphoric acid, ppm) δ: a bis(2-methylphenyl)(6-methyl-3-sulfonatophenyl)phosphine triethylammonium salt as a mono-form showed a peak at −28.12, a bis(6-methyl-3-sulfonatophenyl)(2-methylphenyl)phosphine 2 triethylammonium salt as a di-form showed a peak at −25.00, and a tris(6-methyl-3-sulfonatophenyl)phosphine 3 triethylammonium salt as a tri-form showed a peak at −19.98.

The acquisition 3 was a mixture including 2.3 g (4.7 mmol, 4.73% by mole) of a bis(2-methylphenyl)(6-methyl-3-sulfonatophenyl)phosphine triethylammonium salt, 55.5 g (83.2 mmol, 82.99% by mole) of a bis(6-methyl-3-sulfonatophenyl)(2-methylphenyl)phosphine 2 triethylammonium salt, and 10.4 g (12.3 mmol, 12.28% by mole) of a tris(6-methyl-3-sulfonatophenyl)phosphine 3 triethylammonium salt. From the viewpoint that 68.2 g (100.2 mmol in terms of phosphorous atoms) of the acquisition 3 could be acquired using 50.0 g (106.3 mmol in terms of phosphorous atoms) of the acquisition 2, the yield based on the phosphorous atoms in the conversion step into ammonium salt was 94.3%.

100 g of an aqueous solution including 50% by mass of the acquisition 3 was prepared. Further, the present aqueous solution includes 50.0 g of the acquisition 3 with 73.5 mmol in terms of phosphorous atoms. An aqueous solution of the acquisition 3 was placed in a 3-neck flask having an inner capacity of 300 L, equipped with a thermometer, a stirring device, a dropping funnel, and a nitrogen gas line. To an aqueous solution of the acquisition 3 was added 100 g of the 2-butanone, followed by stirring for 30 minutes, and left to stand for 30 minutes, and an operation of removing a 2-butanone phase was repeated three times. By concentrating the acquired aqueous phase in the range of 35° C. to 70° C. and 4 kPa to 56 kPa to dryness, 41.70 g of a white solid (hereinafter referred to as an acquisition 4) was acquired.

The acquisition was a mixture including 0.50 g (1.02 mmol, 1.69% by mole) of a bis(2-methylphenyl)(6-methyl-3-sulfonatophenyl)phosphine triethylammonium salt, 34.13 g (51.18 mmol, 84.53% by mole) of a bis(6-methyl-3-sulfonatophenyl)(2-methylphenyl)phosphine 2 triethylammonium salt, and 7.08 g (8.34 mmol, 13.78% by mole) of a tris(6-methyl-3-sulfonatophenyl)phosphine 3 triethylammonium salt. From the viewpoint that 41.70 g (60.54 mmol in terms of phosphorous atoms) of an acquisition 4 could be acquired using 50.00 g (73.47 mmol in terms of phosphorous atoms) of the acquisition 3, the yield based on phosphorous atoms in the purification was 82.4%. This acquisition 4 was referred to as a ligand A.

Reference Example 2

The acquisition 3 in Reference Example 1 was a mixture including 4.73% by mole of a bis(2-methylphenyl)(6-methyl-3-sulfonatophenyl)phosphine triethylammonium salt, 82.99% by mole of a bis(6-methyl-3-sulfonatophenyl)(2-methylphenyl)phosphine 2 triethylammonium salt, and 12.28% by mole of a tris(6-methyl-3-sulfonatophenyl)phosphine 3 triethylammonium salt. This phosphorous compound was referred to as a ligand B.

Reference Example 3

The same procedure as in the production of the acquisition 3 in Reference Example 1 except that 86.1 g (243.5 mmol) of tri-n-octylamine was used instead of the triethylamine was carried out, thereby acquiring 123.0 g of a highly viscous pale orange liquid.

$^{31}$P-NMR (400 MHz, 305 K, DMSO-d$_6$, phosphoric acid, ppm) δ: a bis(2-methylphenyl)(6-methyl-3-sulfonatophenyl)phosphine tri-n-octylammonium salt as a mono-form showed a peak at −28.60, a bis(6-methyl-3-sulfonatophenyl)(2-methylphenyl)phosphine 2 tri-n-octylammonium salt as a di-form showed a peak at −25.00, and a tris(6-methyl-3-sulfonatophenyl)phosphine 3 tri-n-octylammonium salt as a tri-form showed a peak at −17.67.

The acquisition was a mixture including 3.6 g (4.9 mmol, 4.80% by mole) of a bis(2-methylphenyl)(6-methyl-3-sulfonatophenyl)phosphine tri-n-octylammonium salt, 99.2 g (84.6 mmol, 82.87% by mole) of a bis(6-methyl-3-sulfonatophenyl)(2-methylphenyl)phosphine 2 tri-n-octylammonium salt, 20.2 g (12.6 mmol, 12.33% by mole) of a tris(6-methyl-3-sulfonatophenyl)phosphine 3 tri-n-octylammonium salt. From the viewpoint that 123.0 g (102.1 mmol in terms of phosphorous atoms) of a desired product could be acquired using 50.0 g (106.3 mmol in terms of phosphorous atoms) of the acquisition 2, the yield based on the phosphorous atoms in the conversion step into ammonium salt was 96.0%. This phosphorous compound was referred to as a ligand C.

Reference Example 4

The same procedure as in the production of the acquisition 3 in Reference Example 1 except that 21.20 g (243.23 mmol) of N,N-dimethylisopropylamine was used instead of the triethylamine was carried out, thereby acquiring 67.50 g of a white solid.

$^{31}$P-NMR (400 MHz, 305 K, DMSO-d$_6$, phosphoric acid, ppm) δ: a bis(2-methylphenyl)(6-methyl-3-sulfonatophenyl)phosphine dimethylisopropylammonium salt as a mono-form showed a peak at −28.17, a bis(6-methyl-3-sulfonatophenyl)(2-methylphenyl)phosphine 2 dimethylisopropylammonium salt as a di-form showed a peak at −25.25, and a tris(6-methyl-3-sulfonatophenyl)phosphine 3 tridimethylisopropylammonium salt as a tri-form showed a peak at −21.50.

The acquisition was a mixture including 2.35 g (4.98 mmol, 4.81% by mole) including a bis(2-methylphenyl)(6-methyl-3-sulfonatophenyl)phosphine tridimethylisopropylammonium salt, 54.84 g (85.85 mmol, 82.85% by mole) of a bis(6-methyl-3-sulfonatophenyl)(2-methylphenyl)phosphine 2 tridimethylisopropylammonium salt, and 10.31 g (12.79 mmol, 12.34% by mole) of a tris(6-methyl-3-sulfonatophenyl)phosphine 3 tridimethylisopropylammonium salt. From the viewpoint that 67.50 g (103.62 mmol in terms of phosphorous atoms) of a desired product could be acquired using 50.0 g (106.26 mmol in terms of phosphorous atoms) of the acquisition 2, the yield based on the phosphorous atoms in the conversion step into ammonium salt was 97.5%. This phosphorous compound was referred to as a ligand D.

Reference Example 5

The acquisition 1 in Reference Example 1 was a mixture including 4.75% by mole of a bis(2-methylphenyl)(6-methyl-3-sulfonatophenyl)phosphine sodium salt, 82.99% by mole of a bis(6-methyl-3-sulfonatophenyl)(2-methylphenyl)phosphine disodium salt, and 12.26% by mole of a tris(6-methyl-3-sulfonatophenyl)phosphine trisodium salt. This phosphorous compound was referred to as a ligand E.

Reference Example 6

100 g (249.8 mmol in terms of sulfur trioxide) of fuming sulfuric acid containing 20% by mass of sulfur trioxide was placed in a 4-neck flask having an internal capacity of 200 ml, equipped with a thermometer, a stirring device, a dropping funnel, and a nitrogen gas line, and 15.2 g (49.9 mmol) of TOTP was introduced thereinto for 0.5 hours. Further, the liquid temperature was controlled to a range of 20° C. to 30° C. After completion of the addition, the reaction was carried out at the same temperature for 5 hours.

While controlling the liquid temperature to a range of 20° C. to 30° C., the sulfonated reaction solution was diluted with 500 g of ion exchange water. The aqueous phase was adjusted to pH 8 to pH 9 by adding 400 g of an aqueous 20%-by-mass sodium hydroxide solution. This neutralizing liquid was concentrated to dryness in the range of 38° C. to 70° C. and 4 kPa to 56 kPa. 1100 g of methanol was added to the obtained concentrated solution, followed by naturally filtering, thereby obtaining a filtrate. This filtrate was concentrated to dryness in the range of 15° C. to 50° C. and 4 kPa to 56 kPa, thereby acquiring 17.7 g of a white solid.

A glass-made column (31 mm in diameter and 340 mm in height) filled with 160 g of a strongly acidic cation exchange resin "Dowex G-26" was prepared. 177 g (17.70 g in terms of white solids, 30.65 mmol in terms of phosphorous atoms) of an aqueous solution including 10% by mass of the white solid was allowed to pass through from the upper part of a column to a linear velocity of 9.3 m/hr to 12.5 m/hr.

30.50 g (86.24 mmol) of tri-n-octylamine was added to the acquired aqueous solution, followed by stirring in the range of 20° C. to 30° C. for 1 hour, to carry out a reaction. Thereafter, the reaction solution was concentrated in the range of 35° C. to 70° C. and 4 kPa to 56 kPa, thereby acquiring 41.46 g of a highly viscous pale orange liquid.

The acquisition was a mixture including 10.75 g (9.17 mmol, 32.40% by mole) of a bis(6-methyl-3-sulfonatophenyl)(2-methylphenyl)phosphine 2 tri-n-octylammonium salt as a di-form, and 30.72 g (19.13 mmol, 67.60% by mole) of a tris(6-methyl-3-sulfonatophenyOphosphine 3 tri-n-octylammonium salt as a tri-form. From the viewpoint that 41.46 g (28.30 mmol in terms of phosphorous atoms) of a desired product could be acquired using 15.20 g (49.94 mmol in terms of phosphorous atoms) of TOTP, the yield based on phosphorous atoms was 56.7%. This phosphorous compound was referred to as a ligand F.

Reference Example 7

10 g of concentrated sulfuric acid was placed in a 3-neck flask having an internal capacity of 100 ml, equipped with a thermometer, a stirring device, a dropping funnel, and a nitrogen gas line. The concentrated sulfuric acid was stirred, and 10.00 g (34.44 mmol in terms of phosphorous atoms) of bis(2-methylphenyl)phenylphosphine (hereinafter referred to as a DOTPP) was introduced thereto for 0.5 hours so as to keep the liquid temperature at 30° C. to 35° C. 35.3 g (132.3 mmol in terms of sulfur trioxide) of fuming sulfuric acid containing 30% by mass of sulfur trioxide was added dropwise thereto for 2 hours from the dropping funnel so as to keep the same temperature. After completion of dropwise addition, stirring was continuously performed at a liquid temperature of 30° C. to 35° C. for 8 hours and at 20° C. to 25° C. for 15 hours.

By controlling the liquid temperature to a range of 20° C. to 30° C., the sulfonation reaction solution was diluted with 90 g of ion exchange water. The aqueous phase was adjusted to pH 8 to pH 9 by adding 113 g of an aqueous 30%-by-mass sodium hydroxide solution, and subsequently, 39.0 g of an aqueous 5%-by-mass sodium hydroxide solution. This neutralizing liquid was concentrated in the range of 38° C. to 70° C. and 4 kPa to 56 kPa, and 720 g of methanol was added to the obtained concentrated solution, followed by naturally filtering, thereby obtaining a filtrate. This filtrate was concentrated to dryness in the range of 15° C. to 50° C. and 4 kPa to 56 kPa, thereby acquiring 16.84 g of a white solid.

A glass-made column (31 mm in diameter and 340 mm in height) filled with 50 g of a strongly acidic cation exchange resin "Dowex G-26" was prepared. 168.4 g (16.84 g in terms of white solids and 34.21 mmol in terms of phosphorous atoms) of an aqueous solution including 10% by mass of the above white solid was allowed to pass through from the upper part of a column to a linear velocity of 9.3 m/hr to 12.5 m/hr.

7.5 g (74.3 mmol) of triethylamine was added to the acquired aqueous solution, followed by stirring in the range of 20° C. to 30° C. for 1 hour, to carry out a reaction. Thereafter, the reaction solution was concentrated in the range of 35° C. to 70° C. and 4 kPa to 56 kPa, thereby acquiring 21.21 g of a pale yellow solid.

$^{31}$P-NMR (400 MHz, 305 K, DMSO-$d_6$, phosphoric acid, ppm) δ: a (6-methyl-3-sulfonatophenyl)(2-methylphenyl)phenylphosphine triethylammonium salt as a mono-form showed a peak at −19.81, and a bis(6-methyl-3-sulfonatophenyl)phenylphosphine 2 triethylammonium salt as a di-form showed a peak at −17.02.

The acquisition was a mixture including 0.32 g (0.69 mmol, 2.10% by mole) of a (6-methyl-3-sulfonatophenyl)(2-methylphenyl)phenylphosphine triethylammonium salt and 20.89 g (31.99 mmol, 97.90% by mole) of a bis(6-methyl-3-sulfonatophenyl)phenylphosphine 2 triethylammonium salt. From the viewpoint that 21.21 g (32.68 mmol in terms of phosphorous atoms) of a desired product could be acquired from 10.00 g (34.44 mmol in terms of phosphorous atoms) of DOTPP, the yield based on phosphorous atoms was 94.9%. This phosphorous compound was referred to as a ligand G.

Reference Example 8

80 g (199.8 mmol in terms of sulfur trioxide) of fuming sulfuric acid containing 20% by mass of sulfur trioxide was placed in a 4-neck flask having an internal capacity of 200 ml, equipped with a thermometer, a stirring device, a dropping funnel, and a nitrogen gas line, and 17.3 g (49.9 mmol) of tris(2,5-dimethylphenyl)phosphine (hereinafter referred to as TXTP) was introduced thereinto for 1 hour. Further, the liquid temperature was controlled to a range of 25° C. to 30° C. After completion of the addition, the reaction was carried out at the same temperature for 3 hours.

While controlling the liquid temperature to a range of 25° C. to 30° C., the sulfonated reaction solution was diluted with 500 g of ion exchange water. The resultant was transferred to a separatory funnel and washed with 250 g of toluene, thereby acquiring an aqueous phase. The aqueous phase was adjusted to pH 8 to pH 9 by adding 328 g of an aqueous 20%-by-mass sodium hydroxide solution. This neutralizing liquid was concentrated until the amount of the liquid became 100 g in the range of 38° C. to 70° C. and 4 kPa to 56 kPa. To the obtained concentrated solution was added 1120 g of methanol, followed by naturally filtering, thereby acquiring a filtrate. This filtrate was concentrated to dryness in the range of 15° C. to 50° C. and 4 kPa to 56 kPa, thereby acquiring 27.80 g of a pale yellow solid.

$^{31}$P-NMR (400 MHz, 305 K, DMSO-$d_6$, phosphoric acid, ppm) δ: a bis(2,5-dimethylphenyl)(2,5-dimethyl-3-sulfonatophenyOphosphine sodium salt as a mono-form showed a peak at −28.67, a bis(2,5-dimethyl-3-sulfonatophenyl)(2,5-dimethylphenyl)phosphine disodium salt as a di-form showed a peak at −28.25 ppm, a tris(2,5-dimethyl-3-sulfonatophenyl)phosphine trisodium salt as a tri-form showed a peak at −27.61, and an oxide formed by oxidation of the phosphorous atoms showed a peak at 37.30 and 39.08.

The acquisition was a mixture including 1.96 g (4.36 mmol, 8.84% by mole) of a bis(2,5-dimethylphenyl)(2,5-dimethyl-3-sulfonatophenyl)phosphine sodium salt, 16.67 g (30.28 mmol, 61.39% by mole) of a bis(2,5-dimethyl-3-sulfonatophenyl)(2,5-dimethylphenyl)phosphine disodium salt, 6.03 g (9.23 mmol, 18.72% by mole) of a tris(2,5-dimethyl-3-sulfonatophenyl)phosphine trisodium salt, and 3.15 g (5.45 mmol, 11.05% by mole) of an oxide formed by oxidation of the phosphorous atoms. From the viewpoint that 27.80 g (49.32 mmol in terms of phosphorous atoms) of a desired product could be acquired using 17.30 g (49.90 mmol in terms of phosphorous atoms) of TXTP, the yield based on phosphorous atoms was 98.8%. This phosphorous compound was referred to as a ligand H.

Reference Example 9

120 g (299.8 mmol in terms of sulfur trioxide) of fuming sulfuric acid containing 20% by mass of sulfur trioxide was placed in a 3-neck flask having an internal capacity of 200 ml, equipped with a thermometer, a stirring device, a dropping funnel, and a nitrogen gas line, and 5.10 g (19.44 mmol) of triphenylphosphine (hereinafter referred to as TPP) was added thereto for 1 hour. Further, the liquid temperature was controlled to a range of 25° C. to 30° C. After completion of the addition, the reaction was carried out at the same temperature for 20 hours.

While controlling the liquid temperature to a range of 25° C. to 30° C., the sulfonated reaction solution was diluted with 200 g of ion exchange water. The resultant was transferred to a separatory funnel, and 150 g of toluene and 80 g of triisooctylamine were thoroughly mixed to acquire an organic phase. The organic phase was adjusted to pH 8 to pH 9 by adding 88 g of an aqueous 20%-by-mass sodium hydroxide solution. This neutralizing liquid was concentrated until the liquid amount reached 40 g in the range of 50° C. to 80° C. and 4 kPa to 56 kPa. To the obtained concentrated solution was added 400 g of methanol, followed by naturally filtering, thereby acquiring a filtrate. This filtrate was concentrated to dryness in the range of 15° C. to 50° C. and 4 kPa to 56 kPa, thereby acquiring 6.60 g of a white solid.

The acquisition was a mixture including 2.10 g (4.49 mmol, 35.80% by mole) of a bis(3-sulfonatophenyl)phenylphosphine disodium salt, 3.15 g (5.55 mmol, 44.20% by mole) of a tris(3-sulfonatophenyl)phosphine trisodium salt, and 1.35 g (2.51 mmol, 20.00% by mole) of an oxide formed by oxidation of the phosphorous atoms. From the viewpoint that 6.60 g (12.55 mmol in terms of phosphorous atoms) of a desired product could be acquired using 5.10 g (19.44 mmol in terms of phosphorous atoms) of TPP, the yield based on phosphorous atoms was 64.6%. This phosphorous compound was referred to as a ligand I.

Reference Example 10

110 g of concentrated sulfuric acid was placed in a 3-neck flask having an internal capacity of 200 ml, equipped with a thermometer, a stirring device, a dropping funnel, and a nitrogen gas line. The concentrated sulfuric acid was stirred and 60.00 g (228.75 mmol) of TPP was introduced thereinto for 1 hour so as to keep the liquid temperature at 25° C. 220 g (686.9 mmol in terms of sulfur trioxide) of fuming sulfuric acid containing 25% by mass of sulfur trioxide was added dropwise thereto for 1 hour from the dropping funnel so as to keep the internal temperature at 25° C. After completion of the dropwise addition, stirring was continuously performed at an internal temperature of 25° C. for 12 hours.

The sulfonated reaction solution was added to 1.8 kg of ice water for dilution and transferred to a separatory funnel. Thereafter, 1.5 liters of 4-methyl-2-pentanone was added thereto, followed by thoroughly mixing. The organic phase was acquired and 28.5 g (281.65 mmol) of triethylamine was added dropwise thereto while keeping the liquid temperature at 25° C. This neutralizing liquid was concentrated to about 250 g, followed by extracting with 200 g of water and evaporating water under reduced pressure, thereby obtaining 47.21 g of a white solid.

The acquisition was a mixture including 45.06 g (101.59 mmol, 95.60% by mole) of a diphenyl(3-sulfonatophenyl)phosphine triethylammonium salt and 2.15 g (4.68 mmol, 4.40% by mole) of an oxide formed by oxidation of the phosphorous atoms. From the viewpoint that 47.21 g (106.27 mmol in terms of phosphorous atoms) of a desired product could be acquired using 60.00 g (228.75 mmol in terms of phosphorous atoms) of TPP, the yield based on phosphorous atoms was 46.5%. This phosphorous compound was referred to as a ligand J.

Reference Example 11

80 g (199.8 mmol in terms of sulfur trioxide) of fuming sulfuric acid containing 20% by mass of sulfur trioxide was placed in a 3-neck flask having an internal capacity of 200 ml, equipped with a thermometer, a stirring device, a dropping funnel, and a nitrogen gas line, and 27.65 g (100.07 mmol) of diphenyl(2-methylphenyl)phosphine (hereinafter referred to as a DPOTP) was added thereto for 1 hour. Further, the liquid temperature was controlled to a range of 25° C. to 30° C. After completion of the addition, the reaction was carried out at the same temperature for 2 hours.

While controlling the liquid temperature to a range of 25° C. to 30° C., the reaction solution was diluted with 600 g of ion exchange water and then transferred to a separatory funnel, and 250 g of toluene and 250 g of tetrahydrofuran were added thereto, thereby acquiring an organic phase. To the organic phase was added 20 g of an aqueous 20%-by-mass sodium hydroxide solution to separate the organic phase, thereby acquire a lower phase. The lower phase was concentrated until the liquid amount reached 95 g in the range of 35° C. to 70° C. and 4 kPa to 55 kPa. A precipitate formed by stirring this concentrated solution at 10° C. for 1 hour was collected by filtration by natural filtering, thereby acquiring 23.53 g of a pale yellow solid.

To this acquisition was added 120 g of ion exchange water to obtain an aqueous solution, and then 24 g of an aqueous 50%-by-mass sulfuric acid solution was added dropwise thereto. Further, 70 g of toluene and 70 g of tetrahydrofuran were added thereto, followed by sufficiently mixing, thereby acquiring an organic phase. To the organic phase was added 10.52 g (103.96 mmol) of triethylamine, followed by stirring in the range of 20° C. to 30° C. for 1 hour. This liquid was concentrated until the liquid amount reached 50 g in the range of 35° C. to 70° C. and 4 kPa to 55 kPa. A precipitate formed by stirring this concentrated solution at 10° C. for 1 hour was collected by filtration by natural filtering, thereby acquiring 15.36 g of a pale yellow solid.

$^{31}$P-NMR (400 MHz, 305 K, DMSO-$d_6$, phosphoric acid, ppm) δ: a diphenyl(6-methyl-3-sulfonatophenyl)phosphine triethylammonium salt as a mono-form showed a peak at −13.19, and an oxide formed by oxidation of the phosphorous atoms showed a peak at 28.73.

The acquisition was a mixture including 14.63 g (31.98 mmol, 95.42% by mole) of a diphenyl(6-methyl-3-sulfonatophenyl)phosphine triethylammonium salt and 0.73 g (1.54 mmol, 4.58% by mole) of an oxide formed by oxidation of the phosphorous atoms. From the viewpoint that 15.36 g (33.52 mmol in terms of phosphorous atoms) of a desired product could be acquired using 27.65 g (100.07 mmol in terms of phosphorous atoms) of DPOTP, the yield based on phosphorous atoms was 33.5%. This phosphorous compound was referred to as a ligand K.

Reference Example 12

158.6 g (332.8 mmol in terms of sulfur trioxide) of fuming sulfuric acid containing 16.8% by mass of sulfur trioxide was placed in a 3-neck flask having an internal capacity of 300 mL, equipped with a thermometer, a stirring device, a dropping funnel, and a nitrogen gas line, and 35.03 g (130.54 mmol) of diphenylcyclohexylphosphine (hereinafter referred to as DPCHxP) was introduced thereinto for 1 hour. Further, the liquid temperature was controlled to a range of 25° C. to 30° C. After completion of the addition, the reaction was carried out at 50° C. for 7 hours.

While controlling the liquid temperature to a range of 25° C. to 30° C., the reaction solution was diluted with 480 g of ion exchange water, and then transferred to a separatory funnel, and 250 g of toluene and 60 g of triisooctylamine were added thereto, followed by thoroughly mixing, thereby acquiring an organic phase. The organic phase was separated by adding 330 g of an aqueous 5%-by-mass sodium hydroxide solution to the organic phase. A lower phase was acquired and 76 g of an aqueous 20%-by-mass sulfuric acid solution was added dropwise thereto. Then, 70 g of toluene and 70 g of tetrahydrofuran were added thereto, followed by sufficiently mixing, thereby acquiring an organic phase. To the organic phase was added 15.85 g (156.63 mmol) of triethylamine, followed by stirring in the range of 20° C. to 30° C. for 1 hour. This liquid was concentrated until the liquid amount reached 50 g in the range of 35° C. to 70° C. and 4 kPa to 55 kPa. A precipitate formed by stirring this concentrated solution at 10° C. for 1 hour was collected by filtration through natural filtering, thereby acquiring 5.68 g of a white solid.

$^{31}$P-NMR (400 MHz, 305 K, DMSO-$d_6$, phosphoric acid, ppm) δ: a (3-sulfonatophenyl)phenylcyclohexylphosphine triethylammonium salt as a mono-form showed a peak at −4.49 and an oxide formed by oxidation of the phosphorous atoms showed a peak at 32.76.

The acquisition was a mixture including 5.32 g (11.83 mmol, 93.81% by mole) of a (3-sulfonatophenyl)phenylcyclohexylphosphine triethylammonium salt and 0.36 g (0.78 mmol, 6.19% by mole) of an oxide formed by oxidation of the phosphorous atoms. From the viewpoint that 5.68 g (12.61 mmol in terms of phosphorous atoms) of a desired product could be acquired using 35.03 g (130.54 mmol) of DPCHxP, the yield based on phosphorous atoms was 9.7%. This phosphorous compound was referred to as a ligand L.

The compositional ratios by mole of water-soluble triarylphosphine used in Examples and Comparative Examples, which were produced in Reference Examples, were summarized in Table 2.

TABLE 2

| Reference Example | Phosphorus compound as a raw material | Compositional ratio (% by mole) of sulfonate | | | | Counter cation | Abbreviation |
|---|---|---|---|---|---|---|---|
| | | Mono-form | Di-form | Tri-form | Oxide | | |
| 1 | TOTP | 1.69 | 84.53 | 13.78 | — | $HNEt_3$ | Ligand A |
| 2 | TOTP | 4.73 | 82.99 | 12.28 | — | $HNEt_3$ | Ligand B |
| 3 | TOTP | 4.80 | 82.87 | 12.33 | — | $HNOct_3$ | Ligand C |
| 4 | TOTP | 4.81 | 82.85 | 12.34 | — | $HNMe_2{}^iPr$ | Ligand D |
| 5 | TOTP | 4.75 | 82.99 | 12.26 | — | Na | Ligand E |
| 6 | TOTP | — | 32.40 | 67.60 | — | $HNOct_3$ | Ligand F |
| 7 | DOTPP | 2.10 | 97.90 | — | — | $HNEt_3$ | Ligand G |
| 8 | TXTP | 8.84 | 61.39 | 18.72 | 11.05 | Na | Ligand H |
| 9 | TPP | — | 35.80 | 44.20 | 20.0 | Na | Ligand I |
| 10 | TPP | 95.60 | — | — | 4.40 | $HNEt_3$ | Ligand J |
| 11 | DPOTP | 95.42 | — | — | 4.58 | $HNEt_3$ | Ligand K |
| 12 | DPCHxP | 93.81 | — | — | 6.19 | $HNEt_3$ | Ligand L |

<Telomerization>

In the respective Examples below, the concentrations of the palladium atoms and the phosphorus compounds included in the aqueous phase acquired by an extraction operation were analyzed and quantified by subjecting a wet decomposition product to a polarized Zeeman atomic absorption spectrophotometer (manufactured by Hitachi, Ltd., Z-5300 Type).

In addition, organic materials such as tertiary amines and 2,7-octadien-1-ol included in the telomerization solution or the aqueous phase including the palladium catalyst were analyzed and quantified by gas chromatography under the following measurement conditions.

(Analysis Condition for Gas Chromatography)

Apparatus: GC-14 A (manufactured by Shimadzu Corporation)

Columns used: G-300 (1.2 mm in internal diameter×20 m in length, 2 in thickness), (Goods) manufactured by Chemicals Evaluation, and Research Institute, Japan Analysis condition: an inlet temperature of 220° C. and a detector temperature of 220° C.

Sample injection amount: 0.4

Carrier gas: helium (260 kPa) is passed at 10 mL/minute.

Column temperature: retention at 60° C. for 5 minutes→temperature rising at 10° C./minutes→retention at 220° C. for 9 minutes Detector: hydrogen flame ionization detector (FID)

Example 1

The telomerization was carried out in a batch mode. A 3 L autoclave equipped with a SUS316 electromagnetic induction stirring device including a 96-mL glass-made pressure container for pumping a palladium catalyst, a 96-mL glass-made pressure container for pumping a solvent, and a sampling port was used as a reactor. Further, the reaction was carried out at a stirring rotation speed of 500 rpm, and from the viewpoint that the reaction results at this time were not different from those at 1000 rpm, a sufficient stirring state could be achieved.

17.69 g of a tetrahydrofuran solution including 94.74 mg (palladium atom 0.422 mmol) of palladium acetate (II), and then 21.46 g of an aqueous solution including 1.457 g (2.115 mmol in terms of trivalent phosphorous atoms) of the ligand A were introduced into a glass-made pressure container and stirred for 60 minutes to prepare a palladium catalyst liquid.

30.06 g of distilled water, 80.10 g of triethylamine, 97.50 g of 2,7-octadien-1-ol, and 114.95 g (2.13 mol) of butadiene were put into an autoclave, followed by stirring at 500 rpm in a closed system and warming to 70° C. Thereafter, the palladium catalyst liquid was pumped with carbon dioxide within 10 seconds from the glass-made pressure container, while the total pressure was set to 1.2 MPa (gauge pressure). Further, a time point at which pumping of the palladium catalyst liquid was completed was defined as 0 hour at initiation of reaction.

In addition, the ratio of the trivalent phosphorus atoms to the palladium atoms at a time of preparation of a catalyst was 5.01, and in the telomerization, the amount of the palladium atoms with respect to 1 mol of butadiene was 0.198 mmol, the mass ratio of triethylamine to water was 1.55, and the mass ratio of a mixture of butadiene and 2,7-octadiene-1-ol to water was 4.12.

For the telomerization solution after a predetermined reaction time, the product was quantified by gas chromatography analysis.

The conversion of the butadiene was calculated by the following equation 1. Further, the respective units in the equations are mol.

$$\text{Butadiene conversion (\%)} = 100 \times \left(1 - \frac{\text{Amount of butadiene in reaction solution}}{\text{Amount of butadiene introduced}}\right) \quad \text{(Equation 1)}$$

Examples of the respective products include 2,7-octadien-1-ol, 1,7-octadien-3-ol, 1,3,6-octatriene, 1,3,7-octatriene, 2,4,6-octatriene, and 4-vinylcyclohexene. However, 1,3,6-octatriene, 1,3,7-octatriene, and 2,4,6-octatriene are collectively referred to as octatrienes. The selectivities of the respective products were calculated by the following equation 2. Further, the respective units in the equations are mol.

$$\text{Selectivity of each product (\%)} = 50 \times \frac{\text{Amount of each product in reaction solution}}{\text{Amount of butadiene reacted}} \quad \text{(Equation 2)}$$

The selectivities to high-boiling-point products which could not sufficiently quantified by gas chromatography were calculated by the following equation 3. Further, the respective units in the equations are mol.

Selectivity of high-boiling product (%)=100−(Total sum of selectivities of the respective products, calculated by Equation 2)   (Equation 3)

The butadiene conversion after 8 hours of the reaction was 80.2%, the selectivity for 2,7-octadien-1-ol was 92.7%, the selectivity for 1,7-octadien-3-ol was 3.1%, the selectivity for octatrienes was 2.5%, and the selectivity for the high-boiling-point products was 1.7%. Further, the selectivity for 4-vinylcyclohexene was 0.01% or less.

The autoclave was cooled to 25° C., and an equivalent amount to reaction consumption of water and 330.23 g (a volume at 25° C. of 463.2 mL) of diethyl ether were pumped with carbon dioxide, using a 96-mL glass-made pressure container for pumping a solvent. The mixture was stirred for 1 hour while pressurizing to a total pressure of 3 MPa (gauge pressure) with carbon dioxide. This mixed liquid was transferred to a pressure container equipped with a glass window, which had been pressurized to 3 MPa (gauge pressure) with carbon dioxide using a pump, to carry out phase separation. The aqueous phase was suitably recovered into a glass-made pressure container, which had been pressurized to 1 MPa (gauge pressure) with carbon dioxide, equipped with a pressure container equipped with a glass. The glass-made pressure container was separated and opened at normal pressure, and the weight of the aqueous phase was measured, while the acquired aqueous phase was used for various kinds of analysis.

In addition, the mass ratio of diethyl ether to the telomerization solution was 0.84.

The content of palladium included in the aqueous phase was calculated from the concentration of palladium demonstrated by the analysis with a polarized Zeeman atomic absorption spectrophotometer using a wet decomposition product of the aqueous phase and the weight of the recovered aqueous phase. The recovery of the palladium atoms was calculated by the following equation 4. Further, the units of the respective amounts in the equations are mol.

$$\text{Recovery of palladium atoms (\%)} = \frac{\text{Amount of palladium in aqueous phase}}{\text{Amount of palladium introduced}} \times 100 \quad \text{(Equation 4)}$$

The content of phosphorous included in the aqueous phase was calculated from the concentration of phosphorous as demonstrated by the analysis with a polarized Zeeman atomic absorption spectrophotometer using a wet decomposition product of the aqueous phase and the weight of the recovered aqueous phase. Further, phosphorous is derived from water-soluble triarylphosphine and an oxide thereof, and there is no significant difference in the recoveries of the water-soluble triarylphosphine and an oxide thereof with respect to the aqueous phase. As a result, the recovery of the water-soluble triarylphosphine with respect to the aqueous phase can be calculated from the amount of the phosphorous atoms introduced and the amount of the phosphorous atoms recovered in the aqueous phase. The recovery of the water-soluble triarylphosphine was calculated by the following equation 5. Further, the units of the respective amounts in the equations are mol.

$$\text{Recovery of water-soluble triarylphosphine (\%)} = 100 \times \frac{\text{Amount of phosphorous atoms in aqueous phase}}{\text{Amount of phosphorous atoms introduced}} \quad \text{(Equation 5)}$$

The tertiary amine included in the aqueous phase was quantified by analyzing the aqueous phase using gas chromatography. The recovery of tertiary amine was calculated by the following equation 6. However, the units of the respective amounts in the equations are mol.

$$\text{Recovery of tertiary amine (\%)} = 100 \times \frac{\text{Amount of tertiary amine in aqueous phase}}{\text{Amount of tertiary amine introduced}} \quad \text{(Equation 6)}$$

The recovery of the palladium atoms with respect to the aqueous phase was 88.9%, the recovery of phosphorous atoms was 84.6%, and the recovery of triethylamine was 70.8%. Further, the amount of diethyl ether incorporated into the aqueous phase was 0.1% by mass or less.

Example 2

The same operation as in Example 1 except that 1.440 g (2.116 mmol in terms of trivalent phosphorous atoms) of a ligand B was used instead of the ligand A was carried out. Further, the ratio of the trivalent phosphorous atoms to the palladium atoms at a time of preparing the catalyst was 5.01.

The butadiene conversion after 8 hours of the reaction was 81.6%, the selectivity for 2,7-octadien-1-ol was 92.5%, the selectivity for 1,7-octadien-3-ol was 3.2%, the selectivity for octatrienes was 2.6%, and the selectivity for the high-boiling-point products was 1.7%. Further, the selectivity for 4-vinylcyclohexene was 0.01% or less.

The recovery of the palladium atoms with respect to the aqueous phase was 87.6%, the recovery of phosphorous atoms was 80.7%, and the recovery of triethylamine was 70.1%. Further, the amount of diethyl ether incorporated into the aqueous phase was 0.1% by mass or less.

Example 3

The same operation as in Example 1 except that 2.545 g (2.113 mmol in terms of trivalent phosphorous atoms) of a ligand C was used instead of the ligand A was carried out. Further, the ratio of the trivalent phosphorous atoms to the palladium atoms at a time of preparing the catalyst was 5.01.

The butadiene conversion after 6 hours of the reaction was 74.4%, the selectivity for 2,7-octadien-1-ol was 93.1%, the selectivity for 1,7-octadien-3-ol was 3.1%, the selectivity for octatrienes was 2,7%, and the selectivity for the high-boiling-point products was 1.1%. Further, the selectivity for 4-vinylcyclohexene was 0.01% or less.

The recovery of the palladium atoms with respect to the aqueous phase was 86.9%, the recovery of phosphorous atoms was 76.8%, and the recovery of triethylamine was 76.9%. Further, the amount of diethyl ether incorporated into the aqueous phase was 0.1% by mass or less.

Example 4

The same operation as in Example 1 except that 1.090 g (2.112 mmol in terms of trivalent phosphorous atoms) of a ligand E was used instead of the ligand A was carried out. Further, the ratio of the trivalent phosphorous atoms to the palladium atoms at a time of preparing the catalyst was 5.00.

The butadiene conversion after 11 hours of the reaction was 77.7%, the selectivity for 2,7-octadien-1-ol was 92.4%, the selectivity for 1,7-octadien-3-ol was 4.3%, the selectivity for octatrienes was 2.3%, and the selectivity for the high-boiling-point products was 1.0%. Further, the selectivity for 4-vinylcyclohexene was 0.01% or less.

The recovery of the palladium atoms with respect to the aqueous phase was 73.0%, the recovery of phosphorous atoms was 90.5%, and the recovery of triethylamine was 59.2%. Further, the amount of diethyl ether incorporated into the aqueous phase was 0.1% by mass or less.

Example 5

The same operation as in Example 1 except that 3.079 g (2.102 mmol in terms of trivalent phosphorous atoms) of a ligand F was used instead of the ligand A was carried out. Further, the ratio of the trivalent phosphorous atoms to the palladium atoms at a time of preparing the catalyst was 4.98.

The butadiene conversion after 13 hours of the reaction was 76.9%, the selectivity for 2,7-octadien-1-ol was 90.8%, the selectivity for 1,7-octadien-3-ol was 5.6%, the selectivity for octatrienes was 2.1%, and the selectivity for the high-boiling-point products was 1.5%. Further, the selectivity for 4-vinylcyclohexene was 0.01% or less.

The recovery of the palladium atoms with respect to the aqueous phase was 90.9%, the recovery of phosphorous atoms was 91.8%, and the recovery of triethylamine was 73.6%. Further, the amount of diethyl ether incorporated into the aqueous phase was 0.1% by mass or less.

Example 6

The same operation as in Example 1 except that 1.370 g (2.109 mmol in terms of trivalent phosphorous atoms) of a ligand G was used instead of the ligand A was carried out. Further, the ratio of the trivalent phosphorous atoms to the palladium atoms at a time of preparing the catalyst was 5.00.

The butadiene conversion after 8 hours of the reaction was 77.9%, the selectivity for 2,7-octadien-1-ol was 88.7%, the selectivity for 1,7-octadien-3-ol was 7.4%, the selectivity for octatrienes was 2.1%, the selectivity for 4-vinylcyclohexene was 0.01% or less, and the selectivity for the high-boiling-point products was 1.8%.

The recovery of the palladium atoms with respect to the aqueous phase was 91.3%, the recovery of phosphorous atoms was 90.9%, and the recovery of triethylamine was 83.0%. Further, the amount of diethyl ether incorporated into the aqueous phase was 0.1% by mass or less.

Example 7

The same operation as in Example 1 except that 1.342 g (2.118 mmol in terms of trivalent phosphorous atoms) of a ligand H was used instead of the ligand A was carried out. Further, the ratio of the trivalent phosphorous atoms to the palladium atoms at a time of preparing the catalyst was 5.02.

The butadiene conversion after 7 hours of the reaction was 78.2%, the selectivity for 2,7-octadien-1-ol was 91.6%, the selectivity for 1,7-octadien-3-ol was 3.4%, the selectivity for octatrienes was 2.9%, and the selectivity for the high-boiling-point products was 2.1%. Further, the selectivity for 4-vinylcyclohexene was 0.01% or less.

The recovery of the palladium atoms with respect to the aqueous phase was 67.9%, the recovery of phosphorous atoms was 62.0%, and the recovery of triethylamine was 82.4%. Further, the amount of diethyl ether incorporated into the aqueous phase was 0.1% by mass or less.

Example 8

The same operation as in Example 1 except that 1.382 g (2.102 mmol in terms of trivalent phosphorous atoms) of a ligand I was used instead of the ligand A was carried out. Further, the ratio of the trivalent phosphorous atoms to the palladium atoms at a time of preparing the catalyst was 4.98.

The butadiene conversion after 34 hours of the reaction was 78.9%, the selectivity for 2,7-octadien-1-ol was 87.0%, the selectivity for 1,7-octadien-3-ol was 8.8%, the selectivity for octatrienes was 3.2%, and the selectivity for the high-boiling-point products was 1.0%. Further, the selectivity for 4-vinylcyclohexene was 0.01% or less.

The recovery of the palladium atoms with respect to the aqueous phase was 66.6%, the recovery of phosphorous atoms was 89.8%, and the recovery of triethylamine was 78.5%. Further, the amount of diethyl ether incorporated into the aqueous phase was 0.1% by mass or less.

Comparative Example 1

The same operation as in Example 1 except that 0.985 g (2.120 mmol in terms of trivalent phosphorous atoms) of a ligand J was used instead of the ligand A was carried out. Further, the ratio of the trivalent phosphorous atoms to the palladium atoms at a time of preparing the catalyst was 5.02.

The butadiene conversion after 4 hours of the reaction was 77.6%, the selectivity for 2,7-octadien-1-ol was 88.2%, the selectivity for 1,7-octadien-3-ol was 5.1%, the selectivity for octatrienes was 5.1%, and the selectivity for the high-boiling-point products was 1.6%. Further, the selectivity for 4-vinylcyclohexene was 0.01% or less.

The recovery of the palladium atoms with respect to the aqueous phase was 28.2%, the recovery of phosphorous atoms was 48.8%, and the recovery of triethylamine was 65.5%. Further, the amount of diethyl ether incorporated into the aqueous phase was 0.1% by mass or less.

Comparative Example 2

The same operation as in Example 1 except that 1.015 g (2.113 mmol in terms of trivalent phosphorous atoms) of a ligand K was used instead of the ligand A was carried out. Further, the ratio of the trivalent phosphorous atoms to the palladium atoms at a time of preparing the catalyst was 5.01.

The butadiene conversion after 4 hours of the reaction was 85.0%, the selectivity for 2,7-octadien-1-ol was 88.8%, the selectivity for 1,7-octadien-3-ol was 5.0%, the selectivity for octatrienes was 4.4%, and the selectivity for the high-boiling-point products was 1.8%. Further, the selectivity for 4-vinylcyclohexene was 0.01% or less.

The recovery of the palladium atoms with respect to the aqueous phase was 12.0%, the recovery of phosphorous atoms was 28.3%, and the recovery of triethylamine was 76.5%. Further, the amount of diethyl ether incorporated into the aqueous phase was 0.1% by mass or less.

Comparative Example 3

The same operation as in Example 1 except that 1.015 g (2.113 mmol in terms of trivalent phosphorous atoms) of a ligand L was used instead of the ligand A was carried out. Further, the ratio of the trivalent phosphorous atoms to the palladium atoms at a time of preparing the catalyst was 5.01.

The butadiene conversion after 6 hours of the reaction was 70.7%, the selectivity for 2,7-octadien-1-ol was 87.0%, the selectivity for 1,7-octadien-3-ol was 3.9%, the selectivity for octatrienes was 7.5%, and the selectivity for the high-boiling-point products was 1.6%. Further, the selectivity for 4-vinylcyclohexene was 0.01% or less.

The recovery of the palladium atoms with respect to the aqueous phase was 10.2%, the recovery of phosphorous atoms was 27.9%, and the recovery of triethylamine was 98.5%. Further, the amount of diethyl ether incorporated into the aqueous phase was 0.1% by mass or less.

The telomerization results and the recovery of the palladium catalyst in Examples 1 to 8 and Comparative Examples 1 to 3 are summarized in Table 3.

The ratio of the trivalent phosphorous atoms to the palladium atoms at a time of preparing the catalyst was in the range of 4.98 to 5.02, in the telomerization, the amount of the palladium atoms with respect to 1 mol of butadiene was 0.198 mmol, the mass ratio of triethylamine to water was 1.55, the mass ratio of a combination of butadiene and 2,7-octadien-1-ol to water was 4.12, the reaction temperature was 70° C., and the total pressure was set to 1.2 MPa (gauge pressure) with carbon dioxide.

In the recovery of the palladium catalyst, the mass ratio of diethyl ether to the telomerization solution was 0.84, the phase separation temperature was 20° C., and the total pressure was set to 3.0 MPa (gauge pressure) with carbon dioxide. The main difference in the evaluation is the type of the water-soluble triarylphosphine (ligand).

Furthermore, in Table 3, butadiene is abbreviated as BD, 2,7-octadien-1-ol is abbreviated as ODA, 1,7-octadien-3-ol is abbreviated as IODA, octatrienes are abbreviated as OCT, and high-boiling-point products are abbreviated as HB. In addition, since the selectivity for 4-vinylcyclohexene is 0.01% or less in any system, it is not denoted in the Table.

a sulfonate group of a trialkylamine salt, in which the total number of carbon atoms of a group to one atom of nitrogen is 5 to 24, a high butadiene conversion can be achieved in a short period of time and a high palladium atom recovery and a high phosphorous atom recovery can be achieved.

Next, according to Examples 9 to 11 and Comparative Examples 4 to 12, the effects of a water-soluble triarylphosphine having two or more sulfonate groups in the molecule and the effects of use of a solvent having a dielectric constant of 2 to 18 in the catalyst recovery are demonstrated.

Example 9

The same operation as in Example 1 except that 2.011 g (2.955 mmol in terms of trivalent phosphorous atoms) of a ligand B was used was carried out. The ratio of the trivalent phosphorous atoms to the palladium atoms at a time of preparing the catalyst was 7.00. The butadiene conversion after 8 hours of the reaction was 83.4%, the selectivity for 2,7-octadien-1-ol was 93.0%, the selectivity for 1,7-octadien-3-ol was 3.5%, the selectivity for octatrienes was 2.1%, and the selectivity for the high-boiling-point products was 1.4%. Further, the selectivity for 4-vinylcyclohexene was 0.01% or less.

The aqueous phase was separated at a carbon dioxide pressure of 3 MPa (gauge pressure) using 330.23 g (a volume at 25° C. of 463.2 mL) of diethyl ether. Further, the amount of the recovery solvent used to the telomerization solution in terms of a mass ratio was 0.84/1. The recovery of the palladium atoms with respect to the aqueous phase was 89.9%, the recovery of phosphorous atoms was 75.9%, and the recovery of triethylamine was 73.1%.

Example 10

The same operation as in Example 9 except that 333.50 g (a volume at 25° C. of 463.2 mL) of diisopropyl ether was used instead of diethyl ether was carried out. Further, the amount of the recovery solvent used with respect to the telomerization

TABLE 3

| | | Condition for telomerization | | | Telomerization results | | | | | Recovery (%) of catalyst with respect to aqueous phase | | |
|---|---|---|---|---|---|---|---|---|---|---|---|---|
| | | Ligand | P/Pd atomic ratio | Reaction time (hr) | BD conversion (%) | Selectivity (%) | | | | | | |
| | | | | | | ODA | IODA | OCT | HB | Palladium | Phosphorus | Amine |
| Example | 1 | A | 5.01 | 8 | 80.2 | 92.7 | 3.1 | 2.5 | 1.7 | 88.9 | 84.6 | 70.8 |
| | 2 | B | 5.01 | 8 | 81.6 | 92.5 | 3.2 | 2.6 | 1.7 | 87.6 | 80.7 | 70.1 |
| | 3 | C | 5.01 | 6 | 74.4 | 93.1 | 3.1 | 2.7 | 1.1 | 86.9 | 76.8 | 76.9 |
| | 4 | E | 5.00 | 11 | 77.7 | 92.4 | 4.3 | 2.3 | 1.0 | 73.0 | 90.5 | 59.2 |
| | 5 | F | 4.98 | 13 | 76.9 | 90.8 | 5.6 | 2.1 | 1.5 | 90.9 | 91.8 | 73.6 |
| | 6 | G | 5.00 | 8 | 77.9 | 88.7 | 7.4 | 2.1 | 1.8 | 91.3 | 90.9 | 83.0 |
| | 7 | H | 5.02 | 7 | 78.2 | 91.6 | 3.4 | 2.9 | 2.1 | 67.9 | 62.0 | 82.4 |
| | 8 | I | 4.98 | 34 | 78.9 | 87.0 | 8.8 | 3.2 | 1.0 | 66.6 | 89.8 | 78.5 |
| Comparative | 1 | J | 5.02 | 4 | 77.6 | 88.2 | 5.1 | 5.1 | 1.6 | 28.2 | 48.8 | 65.5 |
| Example | 2 | K | 5.01 | 4 | 85.0 | 88.8 | 5.0 | 4.4 | 1.8 | 12.0 | 28.3 | 76.5 |
| | 3 | L | 5.01 | 6 | 70.7 | 87.0 | 3.9 | 7.5 | 1.6 | 10.2 | 27.9 | 98.5 |

From Table 3, it can be seen that a high recovery of palladium atoms and a high recovery of phosphorous atoms are achieved by using a water-soluble triarylphosphine having two or more sulfonate groups in the molecule. As shown in Examples 1 to 7, in a case of using a water-soluble triarylphosphine having a methyl group in the meta-position to a phosphorous atom, a higher 2,7-octadien-1-ol selectivity (ODA selectivity) is achieved.

In particular, from Examples 1 to 3, 5, and 6, it is apparent that in a case of using a water-soluble triarylphosphine having solution in terms of a mass ratio was 0.85/1. The recovery of the palladium atoms with respect to the aqueous phase was 91.7%, the recovery of phosphorous atoms was 74.0%, and the recovery of triethylamine was 90.1%.

Example 11

The same operation as in Example 10 except that the aqueous phase was separated at 1.0 MPa (gauge pressure) instead of 3.0 MPa (gauge pressure) of the carbon dioxide pressure was carried out. The recovery of the palladium atoms with respect to the aqueous phase was 90.9%, the recovery of phosphorous atoms was 74.1%, and the recovery of triethylamine was 71.9%.

Comparative Example 4

The same operation as in Example 9 except that 303.40 g (a volume at 25° C. of 463.2 mL) of n-hexane was used instead of diethyl ether was carried out. Further, the amount of the recovery solvent used with respect to the telomerization solution in terms of a mass ratio was 0.78/1. The recovery of the palladium atoms with respect to the aqueous phase was 59.8%, the recovery of phosphorous atoms was 24.7%, and the recovery of triethylamine was 77.2%.

Comparative Example 5

The same operation as in Example 9 except that 372.80 g (a volume at 25° C. of 463.2 mL) of 2-butanone was used instead of diethyl ether was carried out. Further, the amount of the recovery solvent used with respect to the telomerization solution in terms of a mass ratio was 0.96/1. The recovery of the palladium atoms with respect to the aqueous phase was 45.9%, the recovery of phosphorous atoms was 25.3%, and the recovery of triethylamine was 72.4%.

Comparative Example 6

The same operation as in Example 1 except that 285.13 mg (1.270 mmol in terms of palladium atoms) of palladium acetate (II) and 4.130 g (8.89 mmol in terms of trivalent phosphorous atoms) of a ligand J were used was carried out. The ratio of the trivalent phosphorous atoms to the palladium atoms at a time of preparing the catalyst was 7.00. The butadiene conversion after 4 hours of the reaction was 99.6%, the selectivity for 2,7-octadien-1-ol was 86.1%, the selectivity for 1,7-octadien-3-ol was 8.1%, the selectivity for octatrienes was 4.3%, and the selectivity for the high-boiling-point products was 1.5%. Further, the selectivity for 4-vinylcyclohexene was 0.01% or less.

The aqueous phase was separated at a carbon dioxide pressure of 3 MPa (gauge pressure), using 330.23 g (a volume at 25° C. of 463.2 mL) of diethyl ether. Further, the amount of the recovery solvent used with respect to the telomerization solution in terms of a mass ratio was 0.84/1. The recovery of the palladium atoms with respect to the aqueous phase was 28.2%, the recovery of phosphorous atoms was 48.8%, and the recovery of triethylamine was 65.5%.

Comparative Example 7

The same operation as in Comparative Example 6 except that 333.50 g (a volume at 25° C. of 463.2 mL) of diisopropyl ether was used instead of diethyl ether was carried out. Further, the amount of the recovery solvent used with respect to the telomerization solution in terms of a mass ratio was 0.85/1. The recovery of the palladium atoms with respect to the aqueous phase was 27.2%, the recovery of phosphorous atoms was 43.6%, and the recovery of triethylamine was 79.1%.

Comparative Example 8

The same operation as in Comparative Example 6 except that 364.39 g (a volume at 25° C. of 429.7 mL) of 2-methyl tetrahydrofuran was used instead of diethyl ether was carried out. Further, the amount of the recovery solvent used with respect to the telomerization solution in terms of a mass ratio was 0.93/1. The recovery of the palladium atoms with respect to the aqueous phase was 22.6%, the recovery of phosphorous atoms was 40.0%, and the recovery of triethylamine was 84.4%.

Comparative Example 9

The same operation as in Comparative Example 6 except that 379.85 g (a volume at 25° C. of 429.7 mL) of tetrahydrofuran was used instead of diethyl ether was carried out. Further, the amount of the recovery solvent used with respect to the telomerization solution in terms of a mass ratio was 0.97/1. The recovery of the palladium atoms with respect to the aqueous phase was 9.2%, the recovery of phosphorous atoms was 47.4%, and the recovery of triethylamine was 66.3%.

Comparative Example 10

The same operation as in Comparative Example 6 except that 303.40 g (a volume at 25° C. of 463.2 mL) of n-hexane was used instead of diethyl ether was carried out. Further, the amount of the recovery solvent used with respect to the telomerization solution in terms of a mass ratio was 0.78/1. The recovery of the palladium atoms with respect to the aqueous phase was 6.9%, the recovery of phosphorous atoms was 24.1%, and the recovery of triethylamine was 72.6%.

Comparative Example 11

The same operation as in Comparative Example 6 except that 372.80 g (a volume at 25° C. of 463.2 mL) of 2-butanone was used instead of diethyl ether was carried out. Further, the amount of the recovery solvent used with respect to the telomerization solution in terms of a mass ratio was 0.96/1. The recovery of the palladium atoms with respect to the aqueous phase was 5.3%, the recovery of phosphorous atoms was 24.0%, and the recovery of triethylamine was 75.3%.

Comparative Example 12

The same operation as in Comparative Example 6 except that 334.72 g (a volume at 25° C. of 430.9 mL) of acetonitrile was used instead of diethyl ether was carried out. Further, the amount of the recovery solvent used with respect to the telomerization solution in terms of a mass ratio was 0.86/1. The recovery of the palladium atoms with respect to the aqueous phase was 3.5%, the recovery of phosphorous atoms was 3.3%, and the recovery of triethylamine was 49.9%.

The telomerization results and the recovery of the palladium catalyst in Examples 9 to 11 and Comparative Examples 4 to 12 are summarized in Table 4.

The ratio of the trivalent phosphorous atoms to the palladium atoms at a time of preparing the catalyst was 7.00. In the telomerization, the amount of the palladium atoms with respect to 1 mol of butadiene was 0.198 mmol in a case of using the ligand B, and was 0.596 mmol in a case of using the ligand J. The mass ratio of triethylamine to water was 1.61, the mass ratio of a combination of butadiene and 2,7-octadien-1-ol to water was 4.28, the reaction temperature was 70° C., and the total pressure was set to 1.2 MPa (gauge pressure) with carbon dioxide. In the recovery of the palladium catalyst, the mass ratio of the recovery solvent to the telomerization solution was in the range of 0.78/1 to 0.97/1, the phase separation temperature was 20° C., and the total pressure was set to 1.0 MPa to 3.0 MPa (gauge pressure) with carbon dioxide.

The main difference in the evaluation was a type of the recovery solvent. Further, in Table 4, butadiene was abbreviated as BD, 2,7-octadien-1-ol was abbreviated as ODA, 1,7-octadien-3-ol was abbreviated as IODA, octatrienes are abbreviated as OCT, and high-boiling-point products are abbreviated as HB. Diethyl ether was denoted as Et$_2$O, diisopropyl ether was denoted as iPr$_2$O, 2-methyltetrahydrofuran was denoted as MTHF, tetrahydrofuran was denoted as THF, n-hexane was denoted as Hex, 2-butanone was denoted as MEK, and acetonitrile was denoted as AN.

The recovery of the palladium atoms with respect to the aqueous phase was 85.5%, the recovery of phosphorous atoms was 60.7%, and the recovery of triethylamine was 99.8%. Further, the amount of diethyl ether incorporated into the aqueous phase was 0.1% by mass or less.

From these results, it can be seen that in a case of using a tertiary amine having a total number of carbon atoms of 5 to 7 as a tertiary amine, in particular good results can be achieved.

TABLE 4

| | | | Telomerization | | | | | | | Catalyst recovery | | | | |
|---|---|---|---|---|---|---|---|---|---|---|---|---|---|---|
| | | Ligand | Reaction time (hr) | BD conversion (%) | Selectivity (%) | | | Organic solvent | Dielectric constant | Organic solvent/Reaction solution (mass ratio) | Total pressure (MPa) (gauge pressure) | Recovery (%) of catalyst component | | |
| | | | | | ODA | IODA | OCT | HB | | | | | Palladium | Phosphorous | Amine |
| Example | 9 | B | 8 | 83.4 | 93.0 | 3.5 | 2.1 | 1.4 | Et$_2$O | 4.24 | 0.84/1 | 3.0 | 89.9 | 75.9 | 73.1 |
| | 10 | B | 8 | 83.4 | 93.0 | 3.5 | 2.1 | 1.4 | $^i$Pr$_2$O | 3.38 | 0.85/1 | 3.0 | 91.7 | 74.0 | 90.1 |
| | 11 | B | 8 | 83.4 | 93.0 | 3.5 | 2.1 | 1.4 | $^i$Pr$_2$O | 3.38 | 0.85/1 | 1.0 | 90.9 | 74.1 | 71.9 |
| Comparative Example | 4 | B | 8 | 83.4 | 93.0 | 3.5 | 2.1 | 1.4 | Hex | 1.88 | 0.78/1 | 3.0 | 59.8 | 24.7 | 77.2 |
| | 5 | B | 8 | 83.4 | 93.0 | 3.5 | 2.1 | 1.4 | MEK | 18.25 | 0.96/1 | 3.0 | 45.9 | 25.3 | 72.4 |
| | 6 | J | 4 | 99.6 | 86.1 | 8.1 | 4.3 | 1.5 | Et$_2$O | 4.24 | 0.84/1 | 3.0 | 28.2 | 48.8 | 65.5 |
| | 7 | J | 4 | 99.6 | 86.1 | 8.1 | 4.3 | 1.5 | $^i$Pr$_2$O | 3.38 | 0.85/1 | 3.0 | 27.2 | 43.6 | 79.1 |
| | 8 | J | 4 | 99.6 | 86.1 | 8.1 | 4.3 | 1.5 | MTHF | 6.20 | 0.93/1 | 3.0 | 22.6 | 40.0 | 84.4 |
| | 9 | J | 4 | 99.6 | 86.1 | 8.1 | 4.3 | 1.5 | THF | 7.43 | 0.97/1 | 3.0 | 9.2 | 47.4 | 66.3 |
| | 10 | J | 4 | 99.6 | 86.1 | 8.1 | 4.3 | 1.5 | Hex | 1.88 | 0.78/1 | 3.0 | 6.9 | 24.1 | 72.6 |
| | 11 | J | 4 | 99.6 | 86.1 | 8.1 | 4.3 | 1.5 | MEK | 18.25 | 0.96/1 | 3.0 | 5.3 | 24.0 | 75.3 |
| | 12 | J | 4 | 99.6 | 86.1 | 8.1 | 4.3 | 1.5 | AN | 35.69 | 0.86/1 | 3.0 | 3.5 | 3.3 | 49.9 |

According to comparison of Examples 9 to 11 with Comparative Examples 4 and 5, and further, Comparative Examples 6 to 12, it can be seen that in a case of using a solvent having a dielectric constant of 2 to 18, the high recovery of the palladium atoms can be achieved. Particularly, by comparison of Examples 9 and 10 with Comparative Examples 6 and 7, it is apparent that in a case of using a water-soluble triarylphosphine having two or more sulfonate groups in the molecule, a higher palladium atom recovery can be achieved. Further, from Examples 10 and 11, it is apparent that due to a higher carbon dioxide pressure at a time of recovery, a high palladium atom recovery can be achieved.

In Example 12, the telomerization was carried out using a tertiary amine having a total number of carbon atoms of 5 to 7 as a tertiary amine.

Example 12

The same operation as in Example 1 except that 1.375 g (2.111 mmol in terms of trivalent phosphorous atoms) of a ligand D was used instead of 1.457 g (2.115 mmol in terms of trivalent phosphorous atoms) of the ligand A, and 68.99 g (0.792 mol) of N,N-dimethylisopropylamine was used instead of 80.10 g (0.792 mol) of triethylamine was carried out. Further, the ratio of the trivalent phosphorous atoms to the palladium atoms at a time of preparing the catalyst was 5.00, and in the telomerization, the mass ratio of N,N-dimethylisopropylamine to water was 1.34.

The butadiene conversion after 4 hours of the reaction was 90.5%, the selectivity for 2,7-octadien-1-ol was 92.3%, the selectivity for 1,7-octadien-3-ol was 3.3%, the selectivity for octatrienes was 3.3%, and the selectivity for the high-boiling-point products was 1.1%. Further, the selectivity for 4-vinylcyclohexene was 0.01% or less.

According to Example 13, it is demonstrated that an aqueous phase including the palladium catalyst can be reused in the telomerization.

Example 13

To a glass-made pressure container were added a solution formed by dissolving 7.084 g (10.341 mmol) of the ligand B in 19.97 g of water, and a solution formed by dissolving 331.0 mg (1.474 mmol of palladium atoms) of palladium acetate (II) in 38.91 g of triethylammonium, followed by stirring in the range of 20° C.±5° C. for 1 hour, thereby preparing a palladium catalyst liquid.

29.84 g of distilled water, 40.71 g of triethylamine, and 199.84 g (3.695 mol) of butadiene were introduced into an autoclave, followed by stirring at 500 rpm in a closed system and warming to 70° C. Thereafter, the palladium catalyst liquid was pumped with carbon dioxide within 10 seconds from the glass-made pressure container, while the total pressure was set to 1.2 MPa (gauge pressure). Further, a time point at which pumping of the palladium catalyst liquid was completed was defined as 0 hour at initiation of reaction.

Furthermore, the ratio of the trivalent phosphorous atoms to the palladium atoms at a time of preparing the catalyst was 7.02, and in the telomerization, the amount of the palladium atoms with respect to 1 mol of butadiene was 0.399 mmol, the mass ratio of triethylamine to water was 1.60, and the mass ratio of butadiene to water was 4.01.

The conversion of butadiene after 3 hours of the reaction was 60.0%, the selectivity for 2,7-octadien-1-ol was 91.0%, the selectivity for 1,7-octadien-3-ol was 4.4%, the selectivity for octatrienes was 4.1%, and the selectivity for the high-boiling-point products was 0.5%. Further, the selectivity for 4-vinylcyclohexene was 0.01% or less.

The autoclave was cooled to 25° C., and a reaction consumption equivalent of water and 322.59 g of diisopropyl ether were pumped with carbon dioxide, using a 96-mL glass-made pressure container for pumping a solvent. The mixture was stirred at 60° C. for 1 hour while pressurizing to a total pressure of 1.2 MPa (gauge pressure) with carbon dioxide. This mixed liquid was transferred to a pressure container equipped with a glass window, which had been pressurized to 1.0 MPa (gauge pressure) with carbon dioxide using a pump, to carry out phase separation at 10° C.±3° C. The aqueous phase was recovered into the glass-made pressure container, which had been pressurized to 1.0 MPa (gauge pressure) with carbon dioxide, bonded to the pressure container equipped with a glass window.

55.16 g of water was added to the organic phase remaining in the pressure container equipped with a glass window, followed by sufficiently mixing, to carry out phase separation at 10° C.±3° C., and the above aqueous phase was added to the glass-made pressure container, which had been pressurized to 1.0 MPa (gauge pressure) with carbon dioxide, bonded to the pressure container equipped with a glass window existing therein. This operation was repeated twice, thereby acquiring 301.32 g of an aqueous phase.

The acquired aqueous phase was concentrated under reduced pressure for 4 hours at a liquid temperature of 24° C.±3 C under 10 Torr until its weight reached 37.54 g. Further, the main components of the concentrated solution were the palladium catalyst and water, and 99% by mass or more of triethylamine was evaporated by concentration under reduced pressure. To this concentrated solution was added 19.35 g of water, thereby preparing a recovered catalyst liquid.

40.71 g of triethylamine and 199.84 g (3.695 mol) of butadiene were introduced into an autoclave, followed by stirring at 500 rpm in a closed system and warming to 70° C. Thereafter, the recovered catalyst liquid was pumped with carbon dioxide within 10 seconds from the glass-made pressure container, while the total pressure was set to 1.2 MPa (gauge pressure). Further, a time point at which pumping of the palladium catalyst liquid was completed was defined as 0 hour at initiation of reaction.

The conversion of butadiene after 3 hours of the reaction was 65.1%, the selectivity for 2,7-octadien-1-ol was 90.5%, the selectivity for 1,7-octadien-3-ol was 4.7%, the selectivity for octatrienes was 3.7%, and the selectivity for the high-boiling-point products was 1.1%. Further, the selectivity for 4-vinylcyclohexene was 0.01% or less.

From these results, it is apparent that the aqueous phase including the palladium catalyst can be effectively reused in the telomerization.

According to Example 14, it is shown that the aqueous phase including the palladium catalyst recovered at a total pressure of 0.3 MPa (gauge pressure) can also be reused in the telomerization.

Example 14

The telomerization was carried out under the same conditions as in Example 13. The autoclave was cooled to 25° C., and a reaction consumption equivalent of water and 322.59 g of diisopropyl ether were pumped with carbon dioxide, using a 96-mL glass-made pressure container for pumping a solvent. The mixture was stirred at 60° C. for 1 hour while pressurizing to a total pressure of 0.3 MPa (gauge pressure) with carbon dioxide. This mixed liquid was transferred to a pressure container equipped with a glass window, which had been pressurized to 0.3 MPa (gauge pressure) with carbon dioxide using a pump, to carry out phase separation at 10° C.±3° C. The aqueous phase was recovered into the glass-made pressure container, which had been pressurized to 0.3 MPa (gauge pressure) with carbon dioxide, bonded to the pressure container equipped with a glass window.

55.16 g of water was added to the organic phase remaining in the pressure container equipped with a glass window, followed by sufficiently mixing, to carry out phase separation at 10° C.±3° C., and the above aqueous phase was added to the glass-made pressure container, which had been pressurized to 0.3 MPa (gauge pressure) with carbon dioxide, bonded to the pressure container equipped with a glass window existing therein. This operation was repeated four times, thereby acquiring 500.93 g of an aqueous phase.

The acquired aqueous phase was concentrated under reduced pressure for 4 hours at a liquid temperature of 24° C.±3° C. under 10 Torr until its weight reached 38.97 g. Further, the main components of the concentrated solution were the palladium catalyst and water, and 99% by mass or more of triethylamine was evaporated by concentration under reduced pressure. To this concentrated solution was added 17.92 g of water, thereby preparing a recovered catalyst liquid.

40.71 g of triethylamine and 199.84 g (3.695 mol) of butadiene were introduced into an autoclave, followed by stirring at 500 rpm in a closed system and warming to 70° C. Thereafter, the recovered catalyst liquid was pumped with carbon dioxide within 10 seconds from the glass-made pressure container, while the total pressure was set to 1.2 MPa (gauge pressure). Further, a time point at which pumping of the palladium catalyst liquid was completed was defined as 0 hour at initiation of reaction.

The conversion of butadiene after 4 hours of the reaction was 66.2%, the selectivity for 2,7-octadien-1-ol was 90.4%, the selectivity for 1,7-octadien-3-ol was 4.8%, the selectivity for octatrienes was 3.6%, and the selectivity for the high-boiling-point products was 1.2%. Further, the selectivity for 4-vinylcyclohexene was 0.01% or less.

From these results, it is apparent that the aqueous phase including the palladium catalyst recovered at a total pressure of 0.3 MPa (gauge pressure) can be effectively reused in the telomerization.

INDUSTRIAL APPLICABILITY

Since the 2,7-octadien-1-ol obtained by the production method of the present invention can be derived into 7-octenal by isomerization using a copper-based catalyst, the 2,7-octadien-1-ol is useful as a raw material for 7-octenal. The 7-octenal is a compound having a high-reactivity terminal double bond and an aldehyde group, and is useful as a raw material for various industrial chemicals. Specifically, 1,9-nonanedial is produced by subjecting the 7-octenal to a hydroformylation reaction, followed by carrying out a reductive amination reaction, thereby producing 1,9-nonanediamine which is useful as a monomer raw material for polymer.

The invention claimed is:

1. A method for producing 2,7-octadien-1-ol, comprising:
    subjecting butadiene and water to a telomerization in the presence of a palladium catalyst, a tertiary amine and carbon dioxide, the palladium catalyst comprising a water-soluble triarylphosphine and a palladium compound, the water-soluble triarylphosphine comprising two or more sulfonate groups;
    mixing a telomerization solution obtained by the telomerization with an organic solvent having a dielectric constant of 2 to 18 at 25° C. to form a liquid having an aqueous phase and an organic phase; and carrying out phase separation of the liquid in the presence of carbon dioxide by recovering the 2,7-octadien-1-ol from the organic phase while retaining the palladium catalyst in the aqueous phase.

2. The method of according to claim 1, wherein the water-soluble triarylphosphine is represented by the following general formula (I):

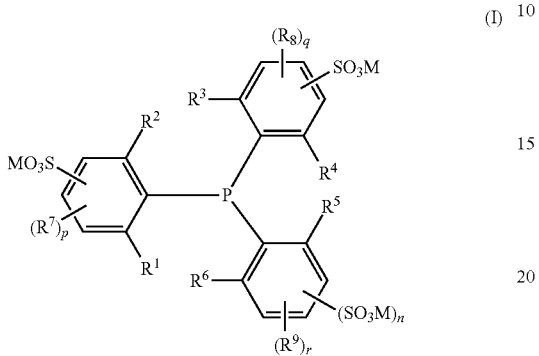

wherein:
$R^1$, $R^2$, $R^3$, $R^4$, $R^5$, and $R^6$ each independently represent a hydrogen atom, an alkyl group having 1 to 4 carbon atoms, or an alkoxy group having 1 to 4 carbon atoms;
$R^7$, $R^8$, and $R^9$ each independently represent an alkyl group having 1 to 4 carbon atoms or an alkoxy group having 1 to 4 carbon atoms;
p, q, and r each independently represent an integer of 0 to 2;
M's may be the same as or different from each other, and each M represents a cation of a metal atom belonging to Group 1 or an ammonium cation derived from a tertiary amine where the total number of carbon atoms of a group bonded to the nitrogen atom of the tertiary amine is 3 to 27;
n represents 0 or 1; and
sulfonate groups (—$SO_3M$) are each at a meta-binding position or a para-binding position to the phosphorous atom of the water-soluble triarylphosphine.

3. The method according to claim 2, wherein:
$R^1$, $R^3$, $R^5$, $R^7$, $R^8$, and $R^9$ each independently represent a hydrogen atom, a methyl group, or a methoxy group;
$R^2$, $R^4$, and $R^6$ are a hydrogen atom;
M's each independently represent a cation of an alkali metal atom or the ammonium cation derived from a tertiary amine; and
the sulfonate groups (—$SO_3M$) are each at the meta-binding position to the phosphorous atom of the water-soluble triarylphosphine.

4. The method according to claim 2, wherein:
$R^1$, $R^2$, $R^3$, $R^4$, $R^5$, and $R^6$ each independently represent a hydrogen atom, a methyl group, or a methoxy group;
p, q, and r are each 0;
M's each independently represent a cation of a lithium atom, a cation of a sodium atom, a cation of a potassium atom, or the ammonium cation derived from a tertiary amine; and
the sulfonate groups (—$SO_3M$) are each at a diagonal binding position of $R^1$, $R^3$, or $R^5$ on the benzene ring.

5. The method according to claim 4, wherein:
$R^1$, $R^3$, and $R^5$ are all the same as each other and each represent a hydrogen atom or a methyl group;
p, q, and r are each 0, and
M's are the same as each other and each represent a cation of a lithium atom, a cation of a sodium atom, a cation of a potassium atom, or the ammonium cation derived from a tertiary amine.

6. The method according to claim 2, wherein:
at least two of $R^1$, $R^3$, and $R^5$ are each an alkyl group having 1 to 4 carbon atoms or an alkoxy group having 1 to 4 carbon atoms.

7. The method according to claim 6, wherein at least two of $R^1$, $R^3$, and $R^5$ are each a methyl group.

8. The method according to claim 2, wherein M is an ammonium cation derived from a tertiary amine where the total number of carbon atoms of a group bonded to the nitrogen atom of the tertiary amine is 5 to 24.

9. The method according to claim 8, wherein M is an ammonium cation derived from a tertiary amine wherein the total number of carbon atoms of a group bonded to the nitrogen atom of the tertiary amine is 5 to 7.

10. The method according to claim 1, wherein the phase separation is carried out at a temperature of 130° C. or lower and a total pressure, after introduction of carbon dioxide, of 0.1 MPa (gauge pressure) or more.

11. The method according to claim 10, wherein the phase separation is carried out at a temperature of 5° C. to 90° C., and a total pressure, after introduction of carbon dioxide, of 0.5 MPa to 3 MPa (gauge pressure).

12. The method according to claim 1, wherein the telomerization is carried out at a temperature of 130° C. or lower and a total pressure, after introduction of carbon dioxide, of 0.5 MPa (gauge pressure) or more.

13. The method according to claim 1, wherein at least a part of the palladium catalyst in the aqueous phase is reused in the telomerization.

* * * * *